US010765517B2

(12) United States Patent
Speziali et al.

(10) Patent No.: US 10,765,517 B2
(45) Date of Patent: Sep. 8, 2020

(54) RINGLESS WEB FOR REPAIR OF HEART VALVES

(71) Applicant: NeoChord, Inc., St. Louis Park, MN (US)

(72) Inventors: Giovanni Speziali, St. Louis Park, MN (US); Dave Blaeser, St. Louis Park, MN (US); John Zentgraf, St. Louis Park, MN (US)

(73) Assignee: Neochord, Inc., St. Louis Park, MN (US)

(*) Notice: Subject to any disclaimer, the term of this patent is extended or adjusted under 35 U.S.C. 154(b) by 63 days.

(21) Appl. No.: 15/765,006

(22) PCT Filed: Oct. 3, 2016

(86) PCT No.: PCT/US2016/055108
§ 371 (c)(1),
(2) Date: Mar. 30, 2018

(87) PCT Pub. No.: WO2017/059406
PCT Pub. Date: Apr. 6, 2017

(65) Prior Publication Data
US 2018/0289483 A1    Oct. 11, 2018

Related U.S. Application Data

(60) Provisional application No. 62/235,839, filed on Oct. 1, 2015.

(51) Int. Cl.
*A61F 2/24*       (2006.01)
*A61B 17/00*     (2006.01)
(Continued)

(52) U.S. Cl.
CPC .......... *A61F 2/2454* (2013.01); *A61B 17/00* (2013.01); *A61B 17/06166* (2013.01);
(Continued)

(58) Field of Classification Search
CPC ...... A61F 2/2454; A61F 2/2457; A61F 2/246; A61F 2/2463
See application file for complete search history.

(56) References Cited

U.S. PATENT DOCUMENTS 2,751,908 A    6/1956    Wallace
3,667,474 A    6/1972    Lapkin
(Continued)

FOREIGN PATENT DOCUMENTS

DE    20 2004 017888 U1    5/2005
EP              1039851 B1    7/2005
(Continued)

OTHER PUBLICATIONS

US 6,197,052 B1, 03/2001, Cosgrove (withdrawn)
(Continued)

*Primary Examiner* — Suba Ganesan
(74) *Attorney, Agent, or Firm* — Patterson Thuente Pedersen, P.A.

(57) ABSTRACT

A ringless web is configured to repair heart valve function in patients suffering from degenerative mitral valve regurgitation (DMR) or functional mitral valve regurgitation (FMR). In accordance with various embodiments, a ringless web can be anchored at one or more locations below the valve plane in the ventricle, such as at a papillary muscle, and one or more locations above the valve plane, such as in the valve annulus. A tensioning mechanism connecting the ringless web to one or more of the anchors can be used to adjust a tension of the web such that web restrains the leaflet to prevent prolapse by restricting leaflet motion to the coaptation zone and/or promotes natural coaptation of the valve leaflets.

22 Claims, 14 Drawing Sheets

(51) Int. Cl.
*A61B 17/06* (2006.01)
*A61B 17/04* (2006.01)
*A61F 2/00* (2006.01)

(52) U.S. Cl.
CPC .......... *A61F 2/2463* (2013.01); *A61F 2/2466* (2013.01); *A61B 2017/0417* (2013.01); *A61B 2017/0441* (2013.01); *A61F 2002/0068* (2013.01); *A61F 2220/0016* (2013.01); *A61F 2230/0043* (2013.01); *A61F 2230/0091* (2013.01)

(56) References Cited

U.S. PATENT DOCUMENTS

| | | |
|---|---|---|
| 3,744,062 A | 7/1973 | Parsonnet |
| 3,842,840 A | 10/1974 | Schweizer |
| 4,258,716 A | 3/1981 | Sutherland |
| 4,351,345 A | 9/1982 | Carney |
| 4,935,027 A | 6/1990 | Yoon |
| 4,957,498 A | 9/1990 | Caspari et al. |
| 4,967,498 A | 9/1990 | Caspari |
| 4,960,424 A | 10/1990 | Grooters |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth |
| 5,336,229 A | 8/1994 | Noda |
| 5,383,877 A | 1/1995 | Clarke |
| 5,431,666 A | 7/1995 | Sauder |
| 5,433,723 A | 7/1995 | Lindenberg et al. |
| 5,452,733 A | 9/1995 | Sterman |
| 5,474,519 A | 12/1995 | Bloomer |
| 5,480,424 A | 1/1996 | Cox |
| 5,547,455 A | 8/1996 | McKenna |
| 5,556,411 A | 9/1996 | Taoda |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo |
| 5,665,100 A | 9/1997 | Yoon |
| 5,667,472 A | 9/1997 | Finn |
| 5,667,473 A | 9/1997 | Finn |
| 5,667,478 A | 9/1997 | McFarlin |
| 5,693,091 A | 12/1997 | Larson |
| 5,725,552 A | 3/1998 | Kotula et al. |
| 5,728,113 A | 3/1998 | Sherts |
| 5,762,458 A | 6/1998 | Wang |
| 5,762,613 A | 6/1998 | Sutton |
| 5,766,163 A | 6/1998 | Mueller |
| 5,772,597 A | 6/1998 | Goldberger |
| 5,772,672 A | 6/1998 | Toy |
| 5,785,658 A | 7/1998 | Benaron |
| 5,797,960 A | 8/1998 | Stevens |
| 5,830,231 A | 11/1998 | Gieges |
| 5,839,639 A | 11/1998 | Sauer |
| 5,853,422 A | 12/1998 | Huebsch et al. |
| 5,897,564 A | 4/1999 | Schulze |
| 5,908,428 A | 6/1999 | Scirica |
| 5,908,429 A | 6/1999 | Yoon |
| 5,919,128 A | 7/1999 | Fitch |
| 5,961,440 A | 10/1999 | Schewich |
| 5,972,004 A | 10/1999 | Williamson |
| 5,972,030 A | 10/1999 | Garrison |
| 5,984,939 A | 11/1999 | Yoon |
| 5,993,466 A | 11/1999 | Yoon |
| 6,022,360 A | 2/2000 | Reimels |
| 6,045,497 A | 4/2000 | Schweich |
| 6,050,936 A | 4/2000 | Schweich |
| 6,053,933 A | 4/2000 | Balazs |
| 6,059,715 A | 5/2000 | Schweich |
| 6,077,214 A | 6/2000 | Mortier |
| 6,117,144 A | 9/2000 | Nobles |
| 6,129,683 A | 10/2000 | Sutton |
| 6,149,660 A | 11/2000 | Laufer |
| 6,152,934 A | 11/2000 | Harper |
| 6,162,168 A | 12/2000 | Schweich |
| 6,162,233 A | 12/2000 | Williamson |
| 6,165,119 A | 12/2000 | Schweich |
| 6,165,120 A | 12/2000 | Schweich |
| 6,165,183 A | 12/2000 | Kuehn |
| 6,178,346 B1 | 1/2001 | Amundson |
| 6,183,411 B1 | 2/2001 | Mortier |
| 6,190,357 B1 | 2/2001 | Ferrari |
| 6,214,029 B1 | 4/2001 | Thill et al. |
| 6,234,079 B1 | 5/2001 | Chertkow |
| 6,234,995 B1 | 5/2001 | Peacock |
| 6,245,079 B1 | 6/2001 | Nobles |
| 6,260,552 B1 | 7/2001 | Mortier |
| 6,261,222 B1 | 7/2001 | Schweich |
| 6,264,602 B1 | 7/2001 | Mortier |
| 6,269,819 B1 | 8/2001 | Oz |
| 6,270,508 B1 | 8/2001 | Klieman |
| 6,283,993 B1 | 9/2001 | Cosgrove |
| 6,312,447 B1 | 11/2001 | Grimes |
| 6,332,863 B1 | 12/2001 | Schweich |
| 6,332,864 B1 | 12/2001 | Schweich |
| 6,332,893 B1 | 12/2001 | Mortier |
| 6,355,050 B1 | 3/2002 | Andreas |
| 6,401,720 B1 | 6/2002 | Stevens |
| 6,402,679 B1 | 6/2002 | Mortier |
| 6,402,680 B2 | 6/2002 | Mortier |
| 6,402,781 B1 | 6/2002 | Langberg |
| 6,406,420 B1 | 6/2002 | McCarthy |
| 6,419,626 B1 | 7/2002 | Yoon |
| 6,436,107 B1 | 8/2002 | Wang |
| 6,443,922 B1 | 9/2002 | Roberts |
| 6,451,054 B1 | 9/2002 | Stevens |
| 6,461,366 B1 | 10/2002 | Sequin |
| 6,508,777 B1 | 1/2003 | Macoviak |
| 6,514,194 B2 | 2/2003 | Schweich |
| 6,533,796 B1 | 3/2003 | Sauer |
| 6,537,198 B1 | 3/2003 | Vidlund |
| 6,537,314 B2 | 3/2003 | Langberg |
| 6,551,331 B2 | 4/2003 | Nobles |
| 6,558,416 B2 | 5/2003 | Cosgrove |
| 6,562,052 B2 | 5/2003 | Nobles |
| 6,564,805 B2 | 5/2003 | Garrison |
| 6,582,388 B1 | 6/2003 | Coleman |
| 6,585,727 B1 | 7/2003 | Cashman |
| 6,589,160 B2 | 7/2003 | Schweich |
| 6,602,288 B1 | 8/2003 | Cosgrove |
| 6,616,684 B1 | 9/2003 | Vidlund |
| 6,619,291 B2 | 9/2003 | Hlavka |
| 6,622,730 B2 | 9/2003 | Ekvall |
| 6,626,917 B1 | 9/2003 | Craig |
| 6,626,930 B1 | 9/2003 | Allen |
| 6,629,534 B1 | 10/2003 | Deem |
| 6,629,921 B1 | 10/2003 | Schweich |
| 6,629,984 B1 | 10/2003 | Chan |
| 6,645,205 B2 | 11/2003 | Ginn |
| 6,679,268 B2 | 1/2004 | Stevens |
| 6,692,605 B2 | 2/2004 | Kerr et al. |
| 6,695,866 B1 | 2/2004 | Kuehn |
| 6,709,456 B2 | 3/2004 | Langberg |
| 6,718,985 B2 | 4/2004 | Hlavka |
| 6,723,038 B1 | 4/2004 | Schroeder |
| 6,726,648 B2 | 4/2004 | Kaplon et al. |
| 6,733,509 B2 | 5/2004 | Nobles |
| 6,740,107 B2 | 5/2004 | Loeb |
| 6,746,471 B2 | 6/2004 | Mortier |
| 6,752,713 B2 | 6/2004 | Johnsons |
| 6,752,813 B2 | 6/2004 | Goldfarb |
| 6,755,777 B2 | 6/2004 | Schweich |
| 6,764,510 B2 | 7/2004 | Vidlund |
| 6,770,083 B2 | 8/2004 | Seguin |
| 6,770,084 B1 | 8/2004 | Bain |
| 6,793,618 B2 | 9/2004 | Schweich |
| 6,802,860 B2 | 10/2004 | Cosgrove |
| 6,808,488 B2 | 10/2004 | Mortier |
| 6,810,882 B2 | 11/2004 | Langberg |

(56) References Cited

U.S. PATENT DOCUMENTS

| | | |
|---|---|---|
| 6,840,246 B2 | 1/2005 | Downing |
| 6,858,003 B2 | 2/2005 | Evans |
| 6,875,224 B2 | 4/2005 | Grimes |
| 6,893,448 B2 | 5/2005 | O'Quinn |
| 6,908,424 B2 | 6/2005 | Mortier |
| 6,918,917 B1 | 7/2005 | Nguyen |
| 6,921,407 B2 | 7/2005 | Nguyen |
| 6,929,715 B2 | 8/2005 | Fladda |
| 6,936,054 B2 | 8/2005 | Chu |
| 6,955,175 B2 | 10/2005 | Stevens |
| 6,962,605 B2 | 11/2005 | Cosgrove |
| 6,978,176 B2 | 12/2005 | Lattouf |
| 6,986,775 B2 | 1/2006 | Morales |
| 6,989,028 B2 | 1/2006 | Lashinski |
| 6,991,635 B2 | 1/2006 | Takamoto |
| 6,997,950 B2 | 2/2006 | Chawla |
| 7,004,176 B2 | 2/2006 | Lau |
| 7,004,952 B2 | 2/2006 | Nobles |
| 7,011,669 B2 | 3/2006 | Kimblad |
| 7,044,905 B2 | 5/2006 | Vidlund |
| 7,048,754 B2 | 5/2006 | Martin |
| 7,070,618 B2 | 7/2006 | Streeter |
| 7,077,862 B2 | 7/2006 | Vidlund |
| 7,083,628 B2 | 8/2006 | Bachman |
| 7,083,638 B2 | 8/2006 | Foerster |
| 7,090,686 B2 | 8/2006 | Nobles |
| 7,094,244 B2 | 8/2006 | Schreck |
| 7,100,614 B2 | 9/2006 | Stevens |
| 7,112,207 B2 | 9/2006 | Allen |
| 7,112,219 B2 | 9/2006 | Vidlund |
| 7,118,583 B2 | 10/2006 | O'Quinn |
| 7,122,040 B2 | 10/2006 | Hill |
| 7,160,322 B2 | 1/2007 | Gabbay |
| 7,179,291 B2 | 2/2007 | Rourke |
| 7,186,264 B2 | 3/2007 | Liddicoat |
| 7,189,199 B2 | 3/2007 | McCarthy |
| 7,217,240 B2 | 5/2007 | Snow |
| 7,226,467 B2 | 6/2007 | Lucatero |
| 7,247,134 B2 | 7/2007 | Vidlund |
| 7,250,028 B2 | 7/2007 | Julian |
| 7,288,097 B2 | 10/2007 | Seguin |
| 7,294,148 B2 | 11/2007 | McCarthy |
| 7,381,210 B2 | 6/2008 | Zarbatany |
| 7,464,712 B2 | 12/2008 | Oz |
| 7,563,267 B2 | 7/2009 | Goldfarb |
| 7,563,273 B2 | 7/2009 | Oz |
| 7,604,646 B2 | 10/2009 | Goldfarb |
| 7,608,091 B2 | 10/2009 | Goldfarb |
| 7,635,386 B1 | 12/2009 | Gammie |
| 7,666,204 B2 | 2/2010 | Thornton |
| 7,704,268 B2 | 4/2010 | Chanduszko |
| 7,815,654 B2 | 10/2010 | Chu |
| 7,879,048 B2 | 2/2011 | Bain |
| 7,887,552 B2 | 2/2011 | Bachman |
| 8,016,882 B2 | 9/2011 | Macoviak et al. |
| 8,052,751 B2 | 11/2011 | Aklog et al. |
| 8,142,494 B2 | 3/2012 | Rahdert et al. |
| 8,303,622 B2 | 11/2012 | Alkhatib |
| 8,443,808 B2 | 5/2013 | Brenzel et al. |
| 8,465,500 B2 | 6/2013 | Speziali |
| 8,758,393 B2 | 6/2014 | Zentgraf |
| 8,938,283 B2 | 1/2015 | Zentgraf et al. |
| 9,044,221 B2 | 6/2015 | Zentgraf et al. |
| 9,192,374 B2 | 11/2015 | Zentgraf |
| 2001/0005787 A1 | 6/2001 | Oz |
| 2001/0016675 A1 | 8/2001 | Mortier |
| 2001/0021872 A1 | 9/2001 | Bailey |
| 2002/0013571 A1 | 1/2002 | Goldfarb |
| 2002/0029080 A1 | 3/2002 | Mortier |
| 2002/0049402 A1 | 4/2002 | Peacock |
| 2002/0077524 A1 | 6/2002 | Schweich |
| 2002/0169359 A1 | 11/2002 | McCarthy |
| 2002/0173694 A1 | 11/2002 | Mortier |
| 2002/0183766 A1 | 12/2002 | Seguin |
| 2003/0004562 A1 | 1/2003 | DiCarlo |
| 2003/0032979 A1 | 2/2003 | Mortier |
| 2003/0050529 A1 | 3/2003 | Vidlund |
| 2003/0050693 A1 | 3/2003 | Quijano |
| 2003/0078600 A1 | 4/2003 | O'Quinn |
| 2003/0105519 A1 | 6/2003 | Fasol |
| 2003/0130731 A1 | 7/2003 | Vidlund |
| 2003/0166992 A1 | 9/2003 | Schweich |
| 2003/0167071 A1 | 9/2003 | Vidlund |
| 2003/0171641 A1 | 9/2003 | Schweich |
| 2003/0181928 A1 | 9/2003 | Vidlund |
| 2003/0187457 A1 | 10/2003 | Weber |
| 2003/0195529 A1 | 10/2003 | Takamoto |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin |
| 2004/0044365 A1 | 3/2004 | Bachman |
| 2004/0049207 A1 | 3/2004 | Goldfarb |
| 2004/0049552 A1 | 3/2004 | Motoyama |
| 2004/0087975 A1 | 5/2004 | Lucatero |
| 2004/0087978 A1 | 5/2004 | Velez et al. |
| 2004/0092962 A1 | 5/2004 | Thornton |
| 2004/0097805 A1 | 5/2004 | Verard |
| 2004/0116767 A1 | 6/2004 | Hermann |
| 2004/0122448 A1 | 6/2004 | Levine |
| 2004/0127983 A1 | 7/2004 | Mortier |
| 2004/0133063 A1 | 7/2004 | McCarthy |
| 2004/0167374 A1 | 8/2004 | Schweich |
| 2004/0167539 A1 | 8/2004 | Kuehn |
| 2004/0220593 A1 | 11/2004 | Greenhalgh |
| 2004/0225300 A1 | 11/2004 | Goldfarb |
| 2004/0225304 A1 | 11/2004 | Vidlund |
| 2004/0236353 A1 | 11/2004 | Bain |
| 2004/0236354 A1 | 11/2004 | Seguin |
| 2004/0243229 A1 | 12/2004 | Vidlund |
| 2004/0267083 A1 | 12/2004 | McCarthy |
| 2005/0004665 A1 | 1/2005 | Aklog et al. |
| 2005/0004668 A1 | 1/2005 | Aklog et al. |
| 2005/0021055 A1 | 1/2005 | Toubia |
| 2005/0021056 A1 | 1/2005 | St. Goar |
| 2005/0021057 A1 | 1/2005 | St. Goar |
| 2005/0033446 A1 | 2/2005 | Deem |
| 2005/0038509 A1 | 2/2005 | Ashe |
| 2005/0044365 A1 | 2/2005 | Bachman |
| 2005/0049667 A1 | 3/2005 | Arbefeuille et al. |
| 2005/0065396 A1 | 3/2005 | Mortier |
| 2005/0075723 A1 | 4/2005 | Schroeder |
| 2005/0075727 A1 | 4/2005 | Wheatley |
| 2005/0101975 A1 | 5/2005 | Nguyen |
| 2005/0125011 A1 | 6/2005 | Spence |
| 2005/0131277 A1 | 6/2005 | Schweich |
| 2005/0131533 A1 | 6/2005 | Alfieri |
| 2005/0143620 A1 | 6/2005 | Mortier |
| 2005/0148815 A1 | 7/2005 | Mortier |
| 2005/0149014 A1 | 7/2005 | Hauck |
| 2005/0154402 A1 | 7/2005 | Sauer |
| 2005/0165419 A1 | 7/2005 | Sauer |
| 2005/0171601 A1 | 8/2005 | Cosgrove |
| 2005/0216039 A1 | 9/2005 | Lederman |
| 2005/0240202 A1 | 10/2005 | Shennib |
| 2005/0251187 A1 | 11/2005 | Beane |
| 2006/0020275 A1 | 1/2006 | Goldfarb et al. |
| 2006/0036317 A1 | 2/2006 | Vidlund |
| 2006/0041306 A1 | 2/2006 | Vidlund |
| 2006/0052868 A1 | 3/2006 | Mortier |
| 2006/0058871 A1 | 3/2006 | Zakay |
| 2006/0074484 A1 | 4/2006 | Huber |
| 2006/0074485 A1 | 4/2006 | Realyvasquez |
| 2006/0089671 A1 | 4/2006 | Goldfarb |
| 2006/0100699 A1 | 5/2006 | Vidlund |
| 2006/0127509 A1 | 6/2006 | Eckman |
| 2006/0135993 A1 | 6/2006 | Seguin |
| 2006/0149123 A1 | 7/2006 | Vidlund |
| 2006/0161040 A1 | 7/2006 | McCarthy |
| 2006/0161193 A1 | 7/2006 | Beane |
| 2006/0184203 A1 | 8/2006 | Martin |
| 2006/0195012 A1 | 8/2006 | Mortier |
| 2006/0195134 A1 | 8/2006 | Crittenden |

(56) References Cited

U.S. PATENT DOCUMENTS

| | | |
|---|---|---|
| 2006/0195183 A1 | 8/2006 | Navia et al. |
| 2006/0241340 A1 | 10/2006 | Schroeder |
| 2006/0287657 A1 | 12/2006 | Bachman |
| 2007/0002627 A1 | 1/2007 | Youn |
| 2007/0027451 A1 | 2/2007 | Desinger |
| 2007/0049952 A1 | 3/2007 | Weiss |
| 2007/0050022 A1 | 3/2007 | Vidlund |
| 2007/0055303 A1 | 3/2007 | Vidlund |
| 2007/0088375 A1 | 4/2007 | Beane |
| 2007/0100356 A1 | 5/2007 | Lucatero |
| 2007/0112244 A1 | 5/2007 | McCarthy |
| 2007/0118154 A1 | 5/2007 | Crabtree |
| 2007/0118155 A1 | 5/2007 | Goldfarb |
| 2007/0129737 A1 | 6/2007 | Goldfarb |
| 2007/0179511 A1 | 8/2007 | Paolitto |
| 2007/0197858 A1 | 8/2007 | Goldfarb |
| 2007/0203391 A1 | 8/2007 | Bloom |
| 2007/0232941 A1 | 10/2007 | Rabinovich |
| 2007/0239272 A1 | 10/2007 | Navia |
| 2007/0265643 A1 | 11/2007 | Beane |
| 2007/0299468 A1 | 12/2007 | Viola |
| 2008/0027468 A1 | 1/2008 | Fenton |
| 2008/0051703 A1 | 2/2008 | Thornton |
| 2008/0065011 A1 | 3/2008 | Marchand |
| 2008/0065156 A1 | 3/2008 | Hauser |
| 2008/0065205 A1 | 3/2008 | Nguyen |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb |
| 2008/0167714 A1 | 7/2008 | St. Goar |
| 2008/0183194 A1 | 7/2008 | Goldfarb |
| 2008/0188873 A1 | 8/2008 | Speziali |
| 2008/0195200 A1 | 8/2008 | Vidlund |
| 2008/0208006 A1 | 8/2008 | Farr |
| 2008/0228223 A1 | 9/2008 | Alkhatib |
| 2009/0012354 A1 | 1/2009 | Wood |
| 2009/0082857 A1 | 3/2009 | Lashinski et al. |
| 2009/0105729 A1 | 4/2009 | Zentgraf |
| 2009/0105751 A1 | 4/2009 | Zentgraf |
| 2009/0131880 A1 | 5/2009 | Speziali |
| 2009/0156995 A1 | 6/2009 | Martin |
| 2009/0163934 A1 | 6/2009 | Raschdorf |
| 2009/0177274 A1 | 7/2009 | Scorsin et al. |
| 2009/0259304 A1 | 10/2009 | O'Beirne |
| 2009/0306622 A1 | 12/2009 | Machold et al. |
| 2010/0042147 A1 | 2/2010 | Janovsky et al. |
| 2010/0174297 A1 | 7/2010 | Speziali |
| 2010/0262233 A1 | 10/2010 | He |
| 2012/0157760 A1* | 6/2012 | Aklog .......... A61F 2/2451 600/37 |
| 2012/0197388 A1* | 8/2012 | Khairkhahan ........ A61F 2/246 623/2.11 |
| 2012/0290077 A1 | 11/2012 | Aklog et al. |
| 2012/0323313 A1 | 12/2012 | Seguin |
| 2013/0023985 A1 | 1/2013 | Khairkhahan et al. |
| 2013/0035757 A1 | 2/2013 | Zentgraf et al. |
| 2013/0304197 A1 | 11/2013 | Buchbinder et al. |
| 2014/0039324 A1 | 2/2014 | Speziali |
| 2014/0067054 A1* | 3/2014 | Chau ................ A61F 2/246 623/2.36 |
| 2014/0214159 A1 | 7/2014 | Vidlund et al. |

FOREIGN PATENT DOCUMENTS

| | | |
|---|---|---|
| EP | 1637091 | 3/2006 |
| EP | 1408850 B1 | 9/2009 |
| EP | 1998686 B1 | 9/2009 |
| EP | 1845861 | 11/2009 |
| JP | 06142114 | 5/1994 |
| WO | WO 99/00059 | 1/1999 |
| WO | WO 99/11200 A1 | 3/1999 |
| WO | WO 99/30647 A1 | 6/1999 |
| WO | WO 00/06026 A2 | 2/2000 |
| WO | WO 00/06026 A3 | 2/2000 |
| WO | WO 00/06027 | 2/2000 |
| WO | WO 00/06028 | 2/2000 |
| WO | WO 00/16700 | 3/2000 |
| WO | WO 01/66018 | 9/2001 |
| WO | WO 01/95809 | 12/2001 |
| WO | WO 03/001893 | 1/2003 |
| WO | WO 03/059209 A2 | 7/2003 |
| WO | WO 03/082157 | 10/2003 |
| WO | WO 03/082158 | 10/2003 |
| WO | WO 04/021893 A2 | 3/2004 |
| WO | WO 04/043265 A2 | 5/2004 |
| WO | WO 05/039428 A2 | 5/2005 |
| WO | WO 05/094525 A2 | 10/2005 |
| WO | WO 06/012750 | 2/2006 |
| WO | WO 06/032051 A2 | 3/2006 |
| WO | WO 06/065966 A2 | 6/2006 |
| WO | WO 06/078694 A2 | 7/2006 |
| WO | WO 06/116310 A2 | 11/2006 |
| WO | WO 06/127509 A2 | 11/2006 |
| WO | WO 07/002627 A1 | 1/2007 |
| WO | WO 07/027451 A2 | 3/2007 |
| WO | WO 07/062128 A2 | 5/2007 |
| WO | WO 07/081418 A1 | 7/2007 |
| WO | WO 07/117612 A1 | 10/2007 |
| WO | WO 08/010738 A2 | 1/2008 |
| WO | WO 2008/112237 A2 | 9/2008 |
| WO | WO 09/052528 A2 | 4/2009 |

OTHER PUBLICATIONS

PCT International Search Report and Written Opinion for PCT/US2016/055108 dated Jan. 11, 2017, 12 pages.

European Search Report for EP Application No. 11863521.8, dated Nov. 15, 2015, 10 pages.

PCT International Preliminary Report on Patentability for PCT/US2008/080560, dated Apr. 29, 2010, 7 pages.

European Search Report, EP Application No. 08839048.9, dated Sep. 16, 2010, 7 pages.

Port Access System for Mitral Valve Repair Proves Its Value in Study; MedGadget, Jul. 9, 2009 as available at: http://medgadget.com/archives/2009/07port access system for mitral valve repair proves its value in study.html (7 pages).

Interactive CardioVascular and Thoracic Surgery; Abstracts: Supplemental 3 to vol. 7 (Sep. 2008), 52 pages.

International Search Report and Written Opinion, Application No. PCT/US2008/080560, dated Aug. 25, 2009, 13 pages.

International Search Report, Application No. PCT/US2008/080560, dated Aug. 28, 2009, 2 pages.

Extended European Search Report, Application No. EP 06718728.6, dated Nov. 11, 2009, 7 pages.

PCT Search Report and Written Opinion, Application No. PCT/US06/01699, dated May 6, 2008.

Notification of International Search Report and Written Opinion of the International Searching Authority, Application No. PCT/US2011/067884, dated Jul. 30, 2012, 11 pages.

International Preliminary Report on Patentability, Application No. PCT/US2011/067884, dated Jul. 11, 2013, 5 pages.

* cited by examiner

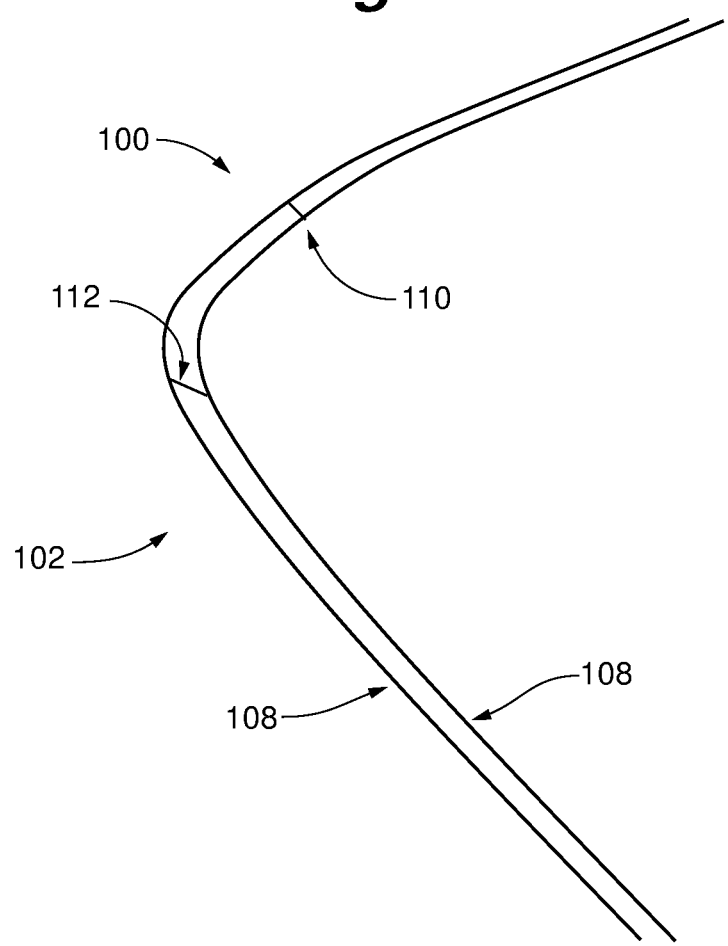

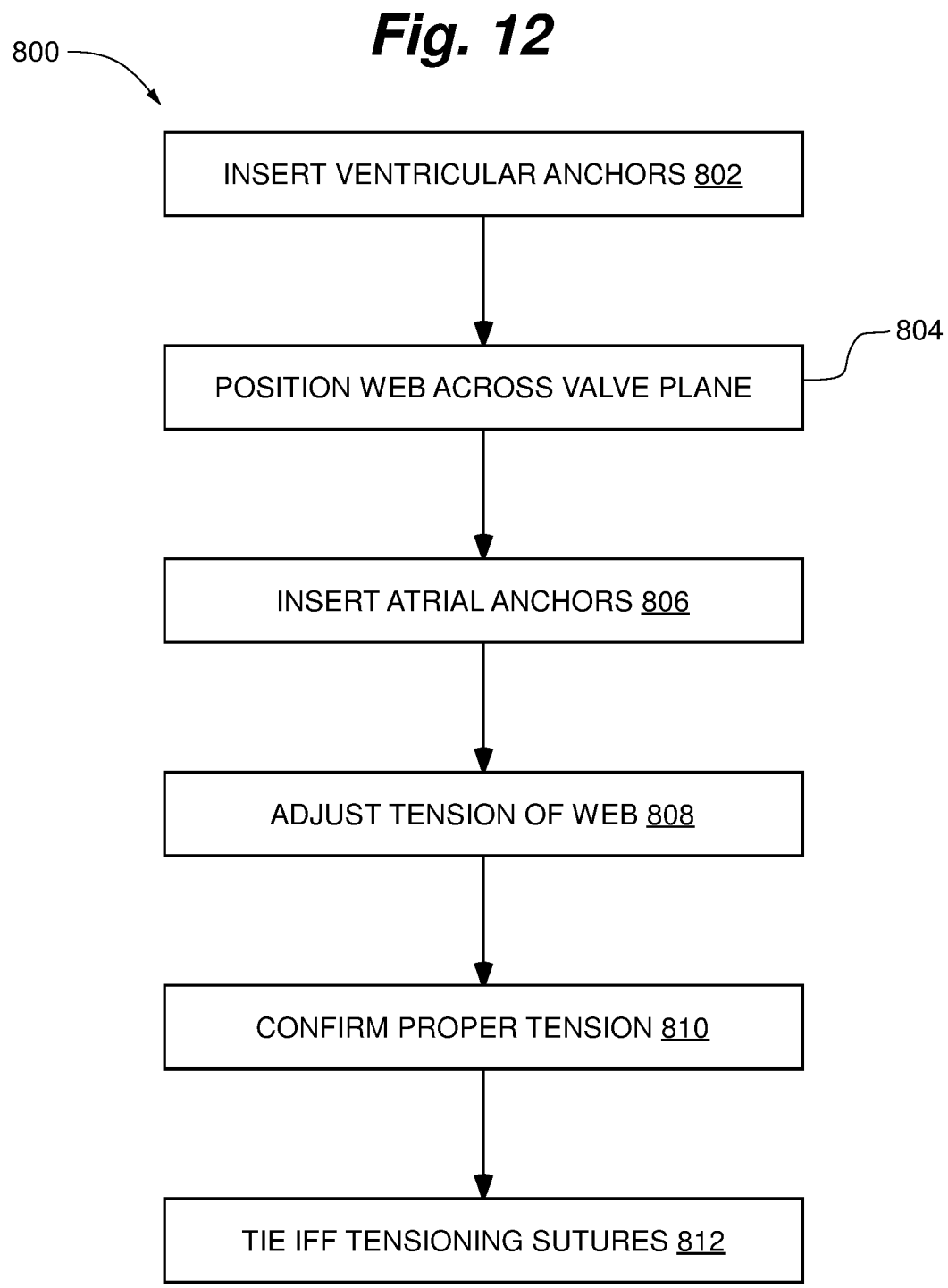

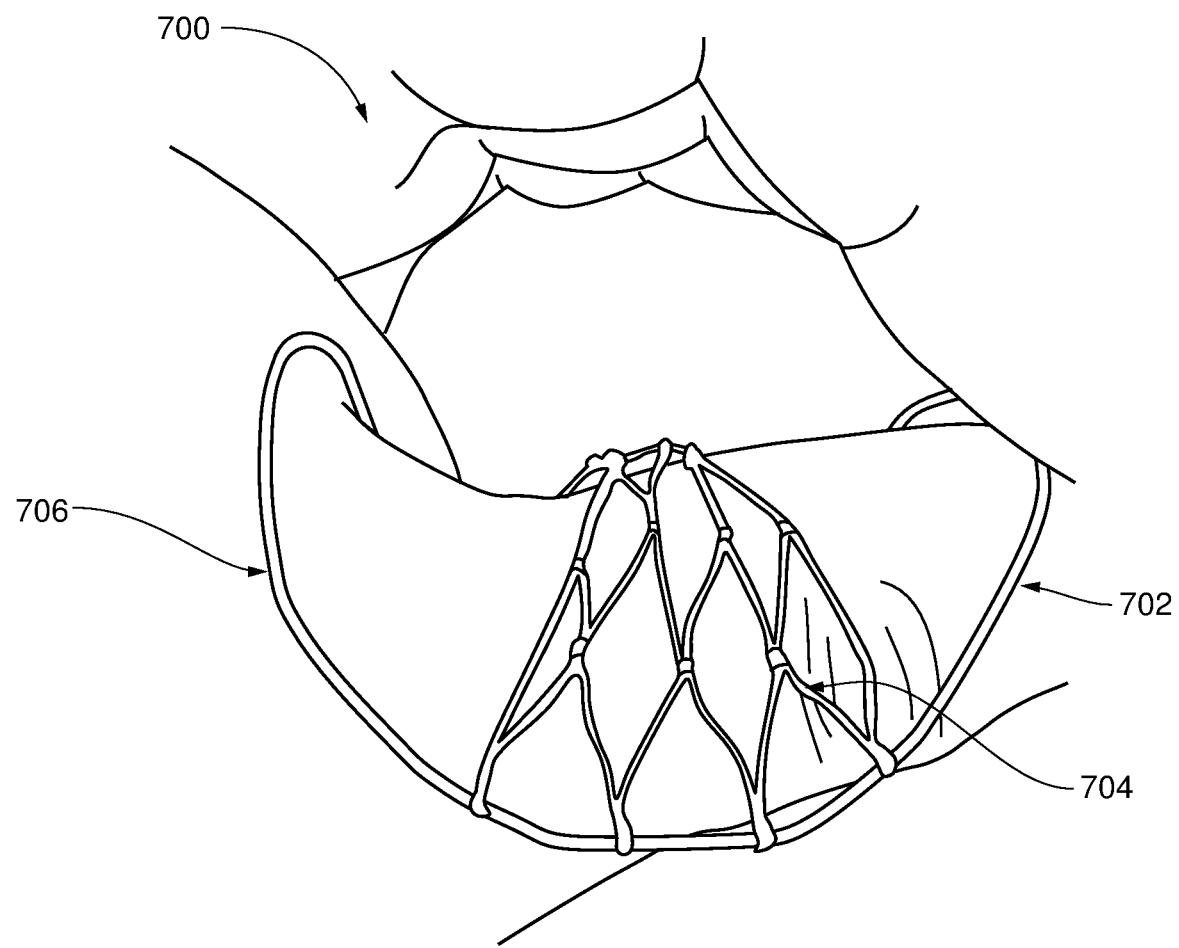

RINGLESS WEB FOR REPAIR OF HEART VALVES

FIELD OF THE INVENTION

The present invention relates to minimally invasive repair of a heart valve. More particularly, the present invention relates to ringless webs for insertion into a beating heart of a patient to repair a heart valve.

BACKGROUND OF THE INVENTION

Various types of surgical procedures are currently performed to investigate, diagnose, and treat diseases of the heart. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or vessels of the heart.

Of particular interest are intracardiac procedures for surgical treatment of heart valves, especially the mitral and aortic valves. Tens of thousands of patients are diagnosed with aortic and mitral valve disease each year. Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts. Valve replacement, however, can present a number of difficulties including that the invasiveness of the procedure can lead to long recovery times and that the irregular shape of the valve annulus can cause difficulty in properly fixing and orienting the replacement valve, which can lead to leaks and other problems. Therefore, in situations where patients can adequately be treating by repairing, rather than replacing, the valve, it is generally preferable to do so.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae, commonly known as degenerative mitral valve regurgitation (DMR), results in partial or generalized leaflet prolapse, which causes mitral (or tricuspid) valve regurgitation. Patients can also suffer from functional mitral valve regurgitation (FMR), in which the chordae, leaflets, and papillary muscles are healthy, but the leaflets still do not properly coapt, causing blood to flow back into the atrium. FMR generally results from left ventricular dilation, which displaces the papillary muscles and stretches the valve annulus.

A number of approaches and devices have been employed to treat leaflet prolapse and/or mitral valve regurgitation. One commonly used technique to surgically correct mitral valve regurgitation is the implantation of artificial chordae (usually 4-0 or 5-0 Gore-Tex sutures) between the prolapsing segment of the leaflet of the valve and the papillary muscle. Another technique involves coapting leaflets together with a clip device and/or suture to prevent leaflet prolapse. Other repair devices, such as spacers and balloons, have been used to provide device-assisted leaflet coaptation to prevent mitral valve regurgitation. However, to date, no specific technique for valve repair has achieved general, broad acceptance in the field as the preferred repair method.

Recent cardiac surgery publications acknowledge the improved patient outcomes delivered with mitral valve repair as compared to mitral valve replacement. One of the factors cited for improved outcomes with mitral valve repair is the preservation of the native mitral valve anatomy. While multiple new technologies are being developed, these technologies are directed towards a target patient population that is very high risk having FMR. It would therefore be desirable to provide for improved valve repair that can be used for patients suffering from DMR as well as patients suffering from FMR.

SUMMARY OF THE INVENTION

A ringless web is configured to repair heart valve function in patients suffering from degenerative mitral valve regurgitation (DMR) or functional mitral valve regurgitation (FMR). In accordance with various embodiments, a ringless web can be anchored at one or more locations below the valve plane in the ventricle, such as at a papillary muscle, and one or more locations above the valve plane, such as in the valve annulus. A tensioning mechanism connecting the ringless web to one or more of the anchors can be used to adjust a tension of the web such that web restrains the leaflet to prevent prolapse by restricting leaflet motion to the coaptation zone and/or promotes natural coaptation of the valve leaflets.

In one embodiment, a ringless web is configured to be chronically implanted into a beating heart of a patient to repair heart valve function. Ringless web can include a web for chronic implantation in the beating heart that is shaped and sized to correspond to at least one valve in the heart. One or more ventricular anchors can be operably connected to the web and configured to be anchored in ventricular tissue in the heart. One or more atrial anchors can be operably connected to the web and configured to be anchored in atrial tissue in the heart. In some embodiments, a tensioning mechanism can be operably connected to one or more of the ventricular anchors and/or one or more of the atrial anchors. The tensioning mechanism can be configured to enable selective adjustment of a tension of the web with respect to the corresponding anchor such that the web is positioned across a plane of the at least one valve to repair valve function. In various embodiments, the web can be formed by, for example, an array, a net or a mesh.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

BRIEF DESCRIPTION OF THE DRAWINGS

The invention may be more completely understood in consideration of the following detailed description of various embodiments of the invention in connection with the accompanying drawings, in which:

FIG. 4B is a side view of the ringless web of FIG. 4A;

FIG. 12 is flowchart depicting a procedure for positioning a ringless web in the heart according to an embodiment of the present invention.

FIGS. 13A-13C depict a heart valve repair device according to an alternative embodiment.

Figure 1:
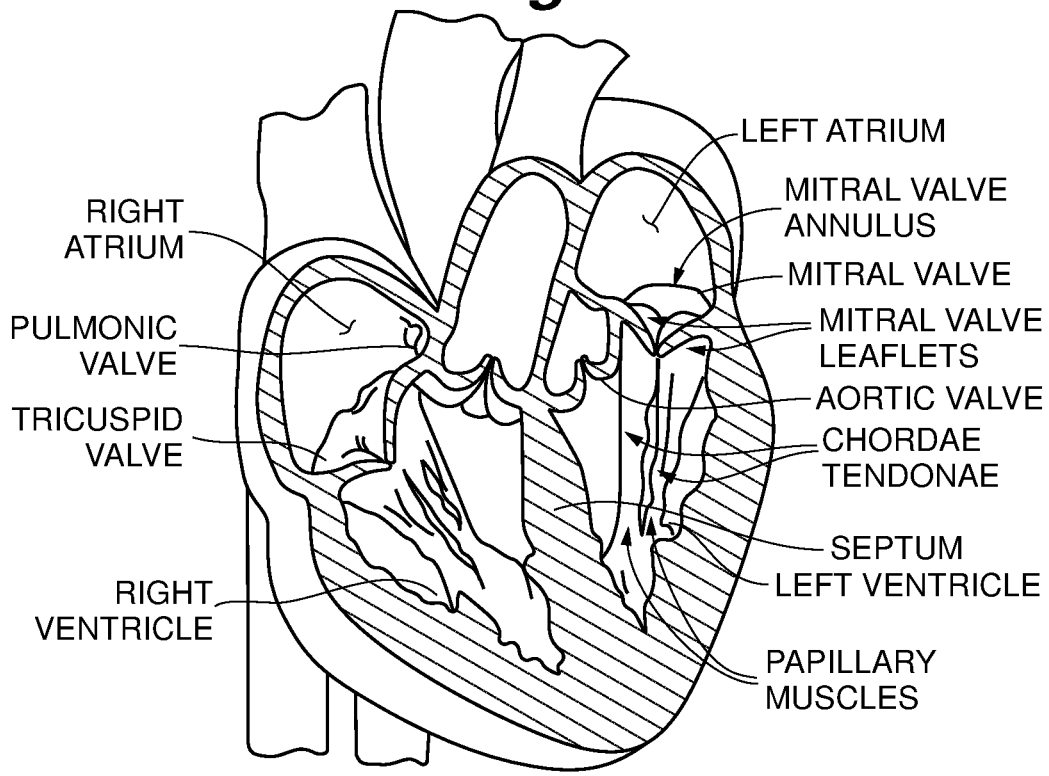
FIG. 1 is a schematic cross-sectional view of a heart.
Figure 2:
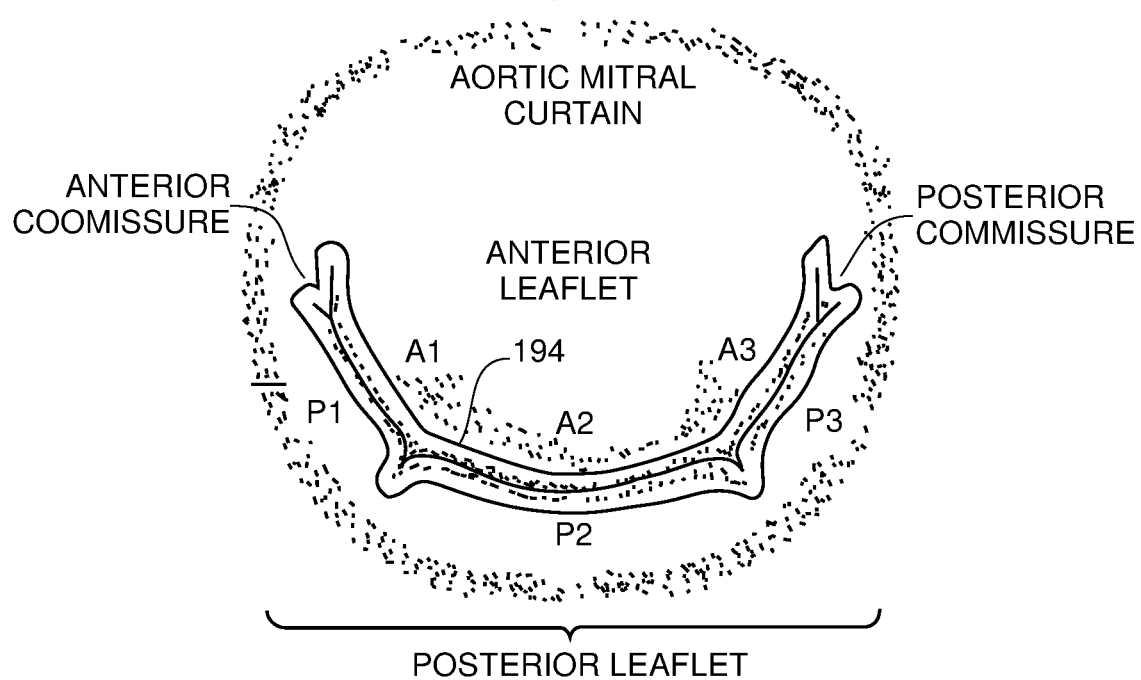
FIG. 2 is a schematic top plan view of a mitral valve.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

A mitral valve is schematically depicted in FIGS. 1-3B. Situated between the left atrium and left ventricle, the mitral valve consists of two flaps of tissue, or leaflets (a posterior leaflet and an anterior leaflet). The mitral valve annulus forms a ring around the valve leaflets, thereby connecting the leaflets to the heart muscle. Papillary muscles are located at the base of the left ventricle. Tendon-like cords called chordae tendineae anchor the mitral valve leaflets to the papillary muscles. Normal chordae tendineae prevent the leaflets from prolapsing, or inverting, into the left atrium, as depicted in FIG. 3A.

Under normal cardiac conditions, the left atrium contracts and forces blood through the mitral valve and into the left ventricle. As the left ventricle contracts, hemodynamic pressure forces the mitral valve shut and blood is pumped through the aortic valve into the aorta. For the mitral valve to shut properly, the valvular edges of the valve leaflets must form a non-prolapsing seal, or coaptation, that prevents the backflow of blood during left ventricular contraction.

Figure 3A:
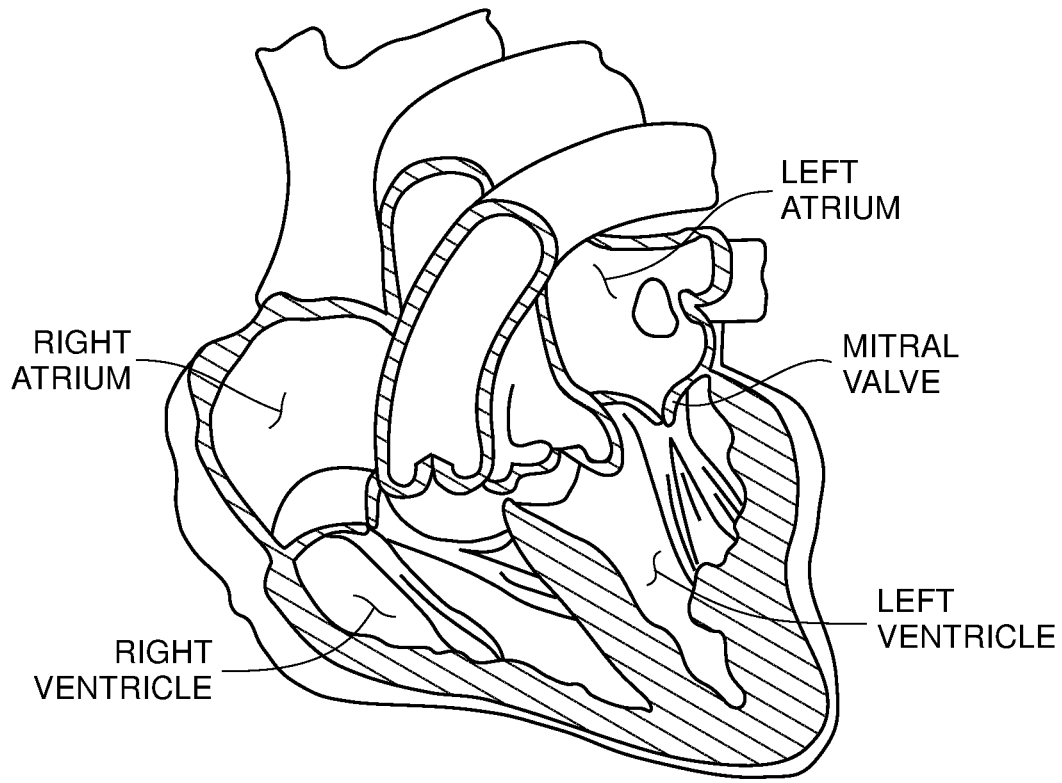
FIG. 3A is a schematic cross-sectional view of a heart with a normal mitral valve.
Figure 3B:
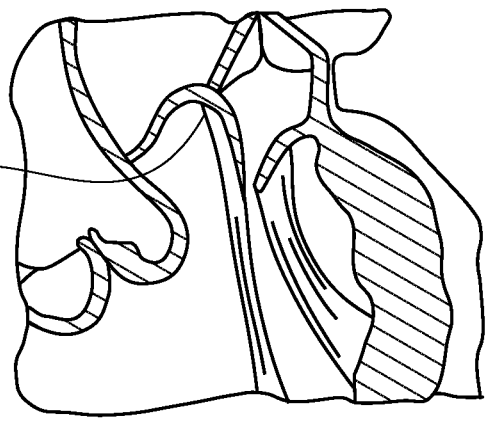
FIG. 3B is a partial schematic cross-sectional view of a heart with an abnormal mitral valve.

A properly functioning mitral valve opens and closes fully. When the mitral valve fails to fully close, as depicted in FIG. 3B, blood from the left ventricle is able to flow backward into the left atrium instead of flowing forward into the aorta. This backflow of blood through the heart valve is called regurgitation. The regurgitation of blood through the heart due to the failure of the mitral valve to close properly (coapt) is the condition known as mitral valve regurgitation (MR). A common symptom of mitral valve regurgitation is congestion of blood within the lungs.

When blood regurgitates from the left ventricle into the left atrium, such as due to MR, less blood is pumped into the aorta and throughout the body. In an attempt to pump adequate blood to meet the blood needs of the body, the left ventricle tends to increase in size over time to compensate for this reduced blood flow. Ventricular enlargement, in turn, often leads to compromised contractions of the heart, thereby exacerbating the congestion of blood within the lungs. If left untreated, severe MR can eventually lead to serious cardiac arrhythmia and/or congestive heart failure (CHF).

Mitral valve regurgitation can be caused by any number of conditions, including mitral valve prolapse (a condition in which the leaflets and chordae tendineae of the mitral valve are weakened resulting in prolapse of the valve leaflets, improper closure of the mitral valve, and the backflow of blood within the heart with each contraction of the left ventricle), damaged chords (wherein the chordae tendineae become stretched or ruptured, causing substantial leakage through the mitral valve), ventricular enlargement (FMR), rheumatic fever (the infection can cause the valve leaflets to thicken, limiting the valve's ability to open, or cause scarring of the leaflets, leading to regurgitation), endocarditis (an infection inside the heart), deterioration of the mitral valve with age, prior heart attack (causing damage to the area of the heart muscle that supports the mitral valve), and a variety of congenital heart defects. As MR becomes exacerbated over time, however, the condition can become more severe, resulting in life-threatening complications, including atrial fibrillation (an irregular heart rhythm in which the atria beat chaotically and rapidly, causing blood clots to develop and break loose and potentially result in a stroke), heart arrhythmias, and congestive heart failure (occurring when the heart becomes unable to pump sufficient blood to meet the body's needs due to the strain on the right side of the heart caused by fluid and pressure build-up in the lungs).

The present application describes various devices that can be implanted into the beating heart of a patient in a minimally invasive manner to treat mitral valve regurgitation as described above. Embodiments of the devices described herein can be used to restrain a prolapsing leaflet to prevent leaflet prolapse in patients suffering from DMR and to promote and retrain natural leaflet coaptation in FMR patients with a minimal device form factor that respects the native valve. In various embodiments, the implantable devices may be adaptable to treat both simple and complex repair requirements including small to large prolapsing or flail segments of primary MR patients (DMR) on either the posterior or anterior leaflets of secondary MR (FMR) patients, as will be described herein.

Figure 4A:
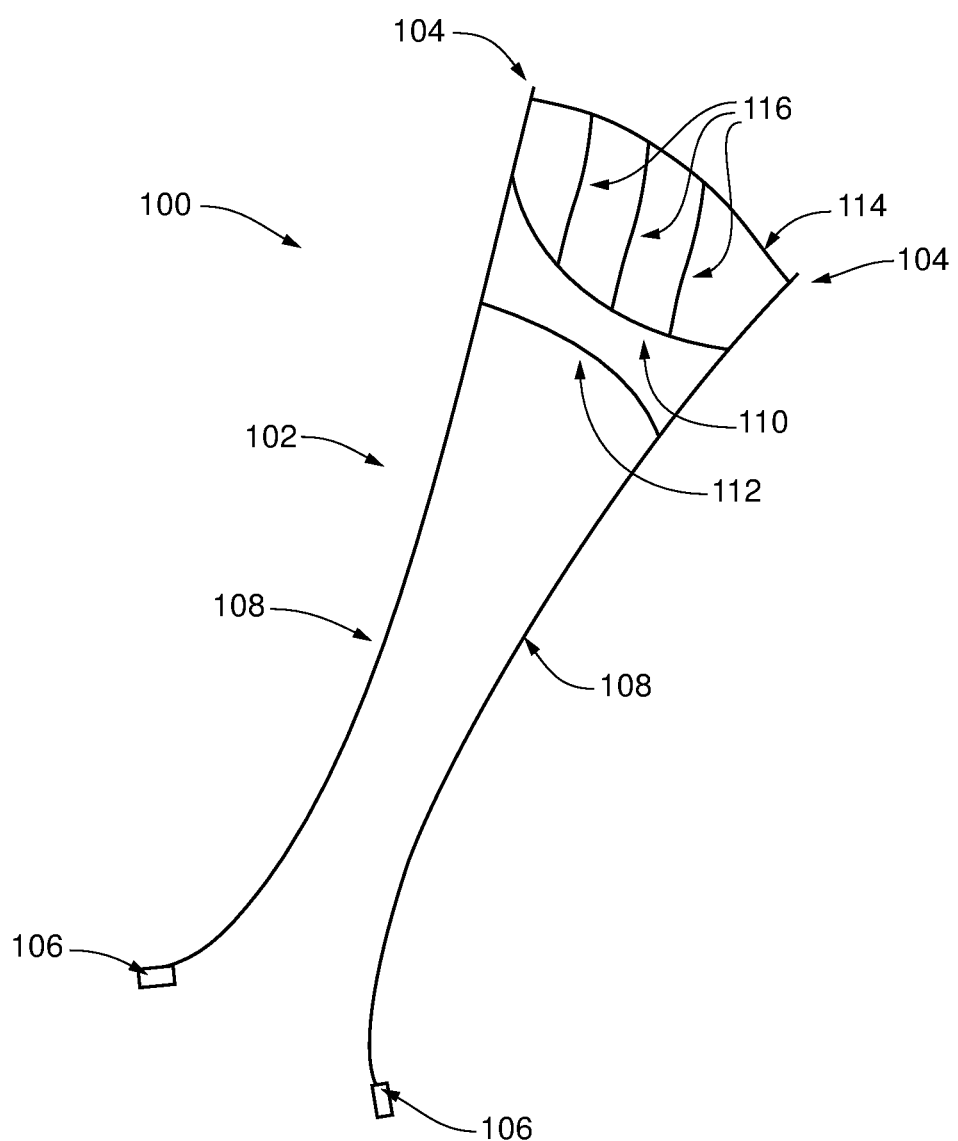
FIG. 4A is a ringless web according to an embodiment of the present invention.

FIGS. 4A and 4B depict one embodiment of a ringless web 100 for treating leaflet prolapse by restraining the leaflet and/or promoting natural coaptation of leaflets according to an embodiment of the present invention. In this embodiment, ringless web 100 comprises an array 102 of intersecting members or struts and multiple anchors that can include one or more atrial anchors 104 and one or more ventricular anchors 106. Array 102 is positioned within the heart to repair the valve and anchors 104 are utilized to maintain the array 102 in the proper position for repair. Web 100 is ringless in that it is secured above the valve plane without being attached to a ring or partial ring seated above the valve plane. Rather, ringless web 100 is anchored in discrete locations above the valve plane via atrial anchors and sutures, as will be described in more detail herein.

As shown in FIGS. 4A and 4B, one embodiment of array 102 can comprise a pair of ventricular struts 108 to extend from anchor points in the atrium above the valve plane, through the coaptation zone of the leaflets and down to anchor points in the left ventricle. Array 102 can also include one or more cross struts, which, in the depicted embodiment, include an upper valve plane strut 110, a lower valve plane strut 112, and an atrial strut 114. In some embodiments, array can further include leaflet struts 116. In some embodiments, a solid biomaterial can be disposed between the upper valve plane strut 110 and lower valve plane strut 112.

The various members or struts of array 102 can be sutures. In various embodiments, struts can be comprised of expanded polytetrafluoroehtylene material or other material suitable for use in the human body. In some embodiments, struts that support the loads applied to the web caused by movement of the leaflets can be comprised of a braided suture material, such as, for example, one or more of the ventricular struts 108, valve plane struts 110, 112, and atrial strut 114. Other struts that contact the leaflets or other valve tissue, such as leaflet struts 116, can be formed of a single suture strand. In some embodiments, struts such as leaflet struts 116 that contact the leaflet or other tissue can have a non-uniform cross-section, such as ovoid, with the portion of the cross-section of greater size positioned to contact the leaflet to distribute the force imparted on the leaflet by the struts to minimize possible damage to the leaflet.

Figure 5A:
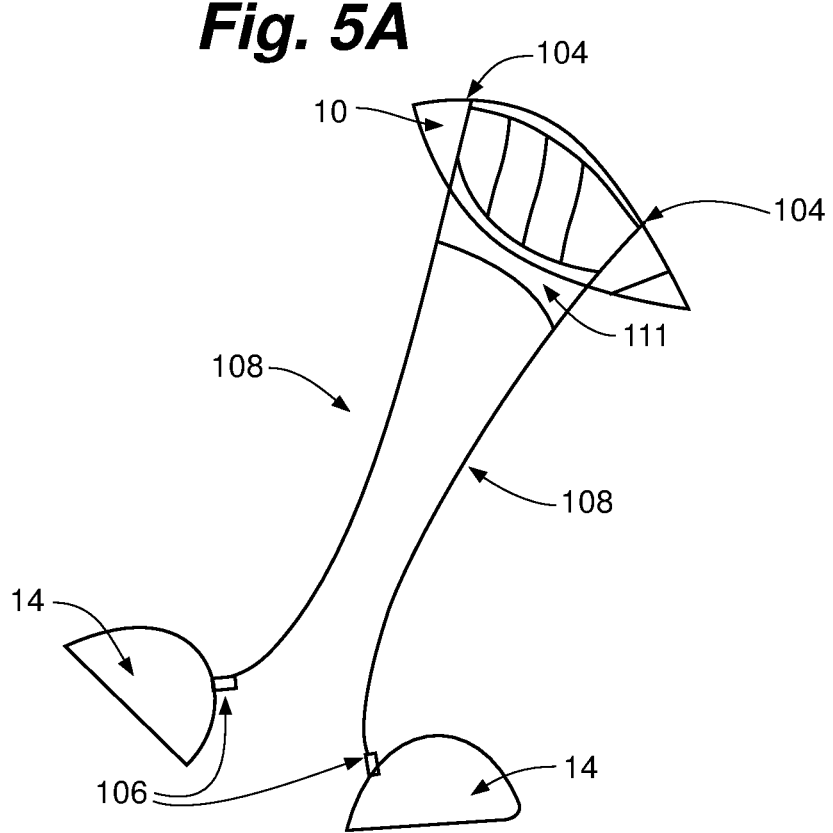
FIGS. 5A and 5B are schematic representations of the ringless web of FIGS. 4A and 4B deployed in the heart.
Figure 5B:
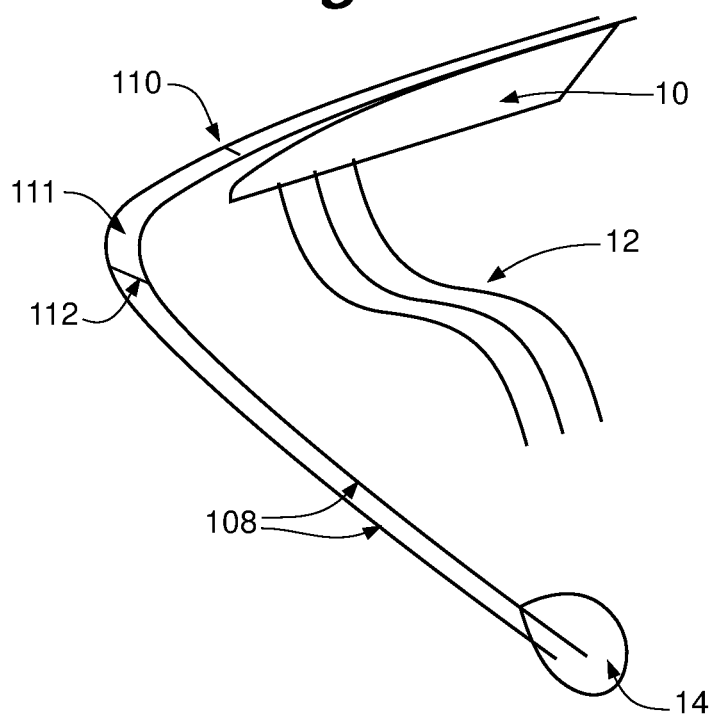

FIGS. 5A and 5B schematically depict ringless web 100 deployed in the heart adjacent a valve leaflet 10, papillary muscles 14, and natural chordae tendinae 12 extending between the valve leaflet 10 and the papillary muscles 14. Leaflet 10 could be either the anterior leaflet or posterior leaflet of the mitral valve, for example. Web 100 can interact with leaflet 10 to restrain the leaflet and restrict leaflet motion to the coaptation zone during systole to prevent the leaflet from prolapsing, which is particularly advantageous in patients suffering from DMR. Atrial anchors 104 are situated in a region above the valve plane in or adjacent to the annulus of the valve. Anchors 104 can be positioned in, for example, the valve annulus, the heart wall adjacent the annulus, or a leaflet adjacent the annulus. Atrial strut 114 can provide support to the web between the atrial anchor 104 points. Ventricular struts 108 extend from the atrial anchors 104, through the valve plane and down into the ventricle where they are anchored with ventricular anchors 106 somewhere in or adjacent to the ventricular wall, such as at the papillary muscles 14. Typically, ventricular anchors 106 are anchored somewhere below a midpoint of the ventricle. In the depicted embodiment, there are two atrial anchors 104 and two ventricular anchors 106, though it should be understood that greater or fewer atrial and/or ventricular anchors can be employed and the numbers of the respective anchors need not be the same. Similarly, the figures depict an embodiment with a pair of ventricular struts 108 that provide redundant support for web, but greater or fewer such struts could be utilized.

As discussed herein, anchoring of the described webs refers to utilization of multiple distinct points of attachment to the wall or muscular structure of the interior chambers of the heart, or, in some embodiments, to a valve leaflet. In some embodiments, one or more anchors are separate devices that are pre-attached to web 100. In other embodiments, one or more anchors can be advanced into the body and utilized to anchor web 100 following deployment of web in the heart. In further embodiments, one or more anchors can be unitarily formed as a single construct with web. Combinations of these embodiments are also contemplated.

As shown in FIGS. 5A and 5B, upper valve plane strut 110 can be positioned above the valve plane and lower valve plane strut 112 can be positioned below the valve plane to offer support on the leaflet and on sub-valvular structure such as the chordae tendinae, respectively, to reduce the load on the ringless web 100 at the atrial anchors 104. Portions of web 100 are therefore positioned both above and below the valve plane. In some embodiments, the region 111 between the valve plane struts 110, 112 that is in the coaptation zone of the leaflets can include a solid biomaterial positioned therein to increase the surface area for leaflet coaptation, which is particularly useful for patients suffering from functional mitral valve regurgitation. In some such embodiments, the use of web 100 in valve to prevent regurgitation ultimately retrains and reshapes the valve such that the valve leaflets and annulus naturally revert to a more natural configuration to obtain proper coaptation over time. In such embodiments, the biomaterial can be a bioabsorbable material that is absorbed into the body over time. Suitable biomaterials can include, for example, bovine pericardium and CardioCel®. Leaflet struts 116 can be positioned to overlay the leaflet to prevent leaflet prolapse.

Figure 6:
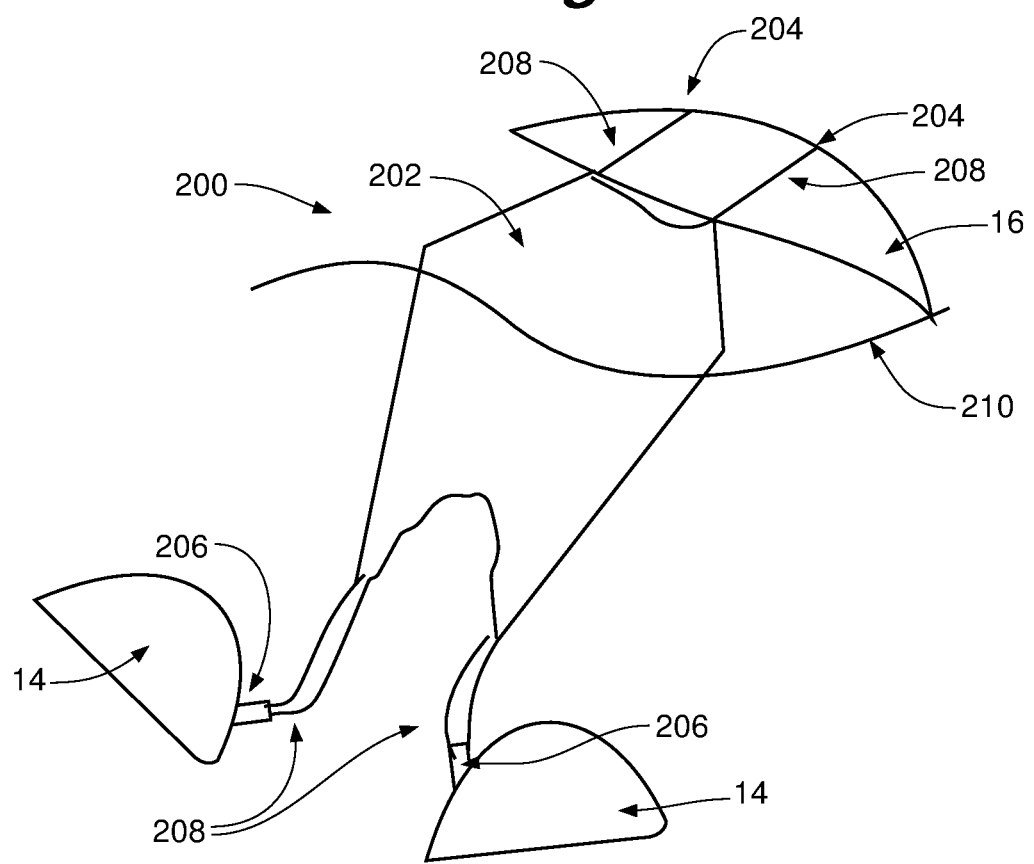
FIG. 6 is a schematic representation of a ringless web according to an embodiment of the present invention deployed in the heart.

FIG. 6 depicts a ringless web 200 according to another embodiment of the present invention deployed in the heart. Ringless web 200 includes a body 202 configured as a dense mesh or net material as opposed to an array of members or struts as described with respect to repair device 100. Similarly to the embodiment described above incorporating a solid biomaterial, web 200 can advantageously be employed to treat patients suffering from FMR. In such cases, the web, which in some embodiments can include or be formed of a bioabsorbable material, can retrain and reshape the valve such that the valve leaflets and annulus naturally revert to a more natural configuration to obtain proper coaptation over time.

Similarly to the previous embodiment, body 202 is positioned within the heart with one or more atrial anchors 204 positioned in or near the valve annulus 16 and one or more ventricular anchors 206 seating in, for example, a papillary muscle 14. Each anchor can be attached to body 202 with one or more sutures 208. Body 202 is positioned to extend across the valve plane 210 through the coaptation zone to provide additional surface area for leaflet coaptation.

As exemplified in the embodiments described herein, ringless webs according to embodiments of the present invention can comprise a variety of different configurations having a variety of different porosities. A "web" as described herein describes a flexible material having a combination of solid material and open space therein and capable of conforming to aspects of the native valve tissue. For example, webs can comprise an array, a net or a mesh, which have decreasing amounts of porosity. In one embodiment, an array can be considered a web having 70-90% open space, a net can 30-75% open space and a mesh can have 10%-30% open space.

Figure 7A:
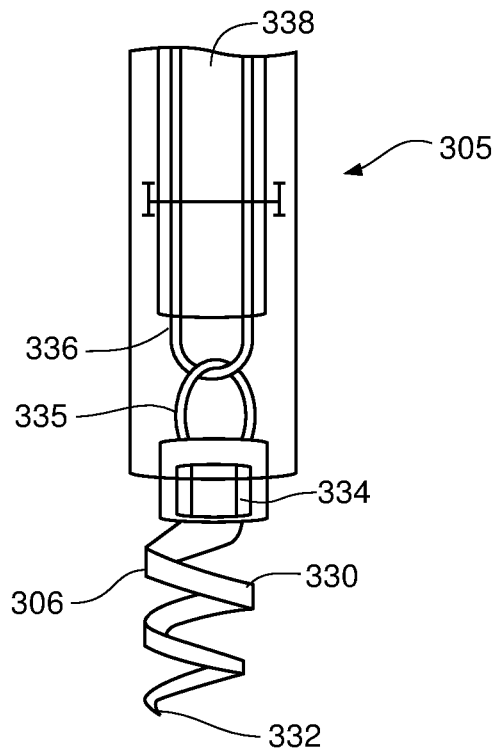
FIGS. 7A-7C depict an anchor system for a ringless web according to an embodiment of the present invention.
Figure 7B:
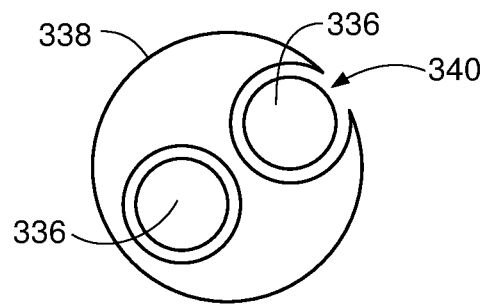
Figure 7C:
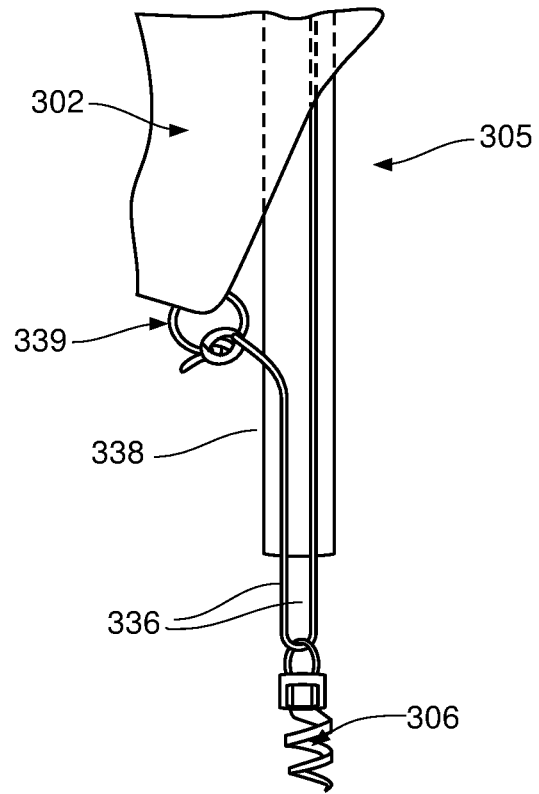

FIGS. 7A-7C depict one embodiment of an anchoring system 305 that can be used with the various ringless web embodiments of the present invention. Anchoring system 305 can be used to implant either atrial anchors or ventricular anchors as described herein. Each of the various embodiments of anchoring systems discussed herein can be used interchangeably such that different anchor embodiments can be used for atrial anchors than for ventricular anchors, as well as using atrial anchors that differ from each other and/or ventricular anchors that differ from each other. In one embodiment, anchoring system 305 implants a ventricular anchor 306 into a papillary muscle. Anchoring systems as described herein can include embodiments in which the anchors are independent of the web repair device with an interconnect existing between the web device and the anchors. Alternatively, anchoring systems can be configured such that the anchors are integrated into and unitary with the web repair device.

Anchoring system 305 includes a soft tissue anchor 306 that can include an anchor portion 330 configured as a corkscrew shape having a sharp distal tip 332 and a head 334. A connector 335 can be attached to head 334 of anchor. In some embodiments, connector 335 can be formed by a loop of suture material. Connector 335 can connect anchor 306 to a tensioning suture 336 that can be looped through the connector 335 and carried by a tensioning catheter 338 as shown in FIG. 7A. Tensioning suture 336 can extend from anchor 306 towards a ringless web 300 and be connected thereto, by, for example, being tied by a surgeon with a knot onto a connecting element such as a ring 339. Tensioning catheter includes a longitudinal opening 340 that enables the tension of tensioning suture 336 to be adjusted after anchor portion 330 has been driven into soft tissue, with head 334 and connector 335 extending from tissue. In this manner, when an anchor 306 is implanted into soft tissue, such as a papillary muscle, tensioning suture 336 can be used to adjust the tension with which the anchor carries a ringless web 300 to ensure proper repair. Proper leaflet function with repair device in place at a given tension can be confirmed via, e.g., an ultrasonic imaging system, prior to tying off the tensioning suture. In other embodiments, ringless webs, anchors, and connecting sutures as described herein can be pre-sized to provide proper valve function or can be conformable to the valve such that tensioning of web with respect to anchors is not required.

Figure 8A:
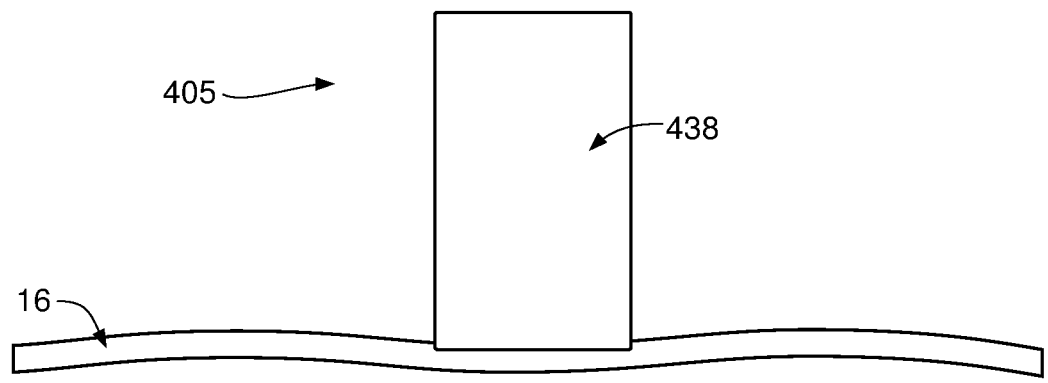
FIGS. 8A-8C depict an anchor system for a ringless web according to an embodiment of the present invention.
Figure 8B:
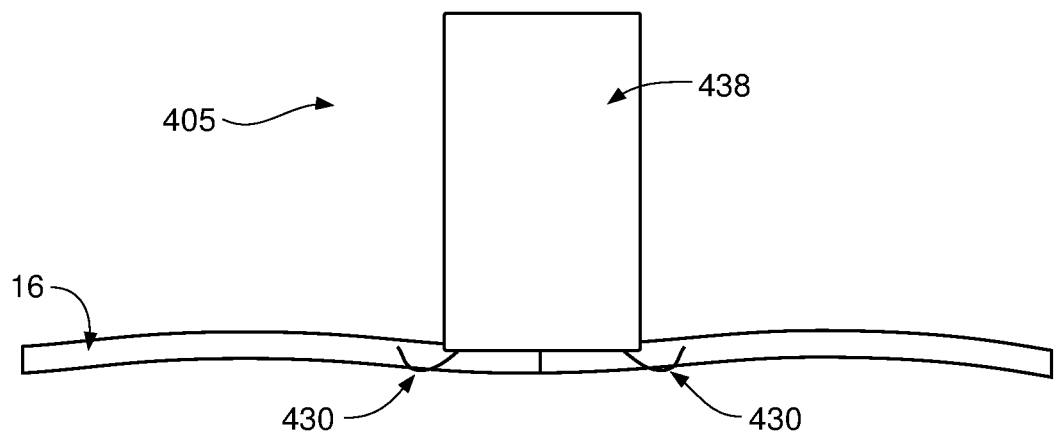
Figure 8C:
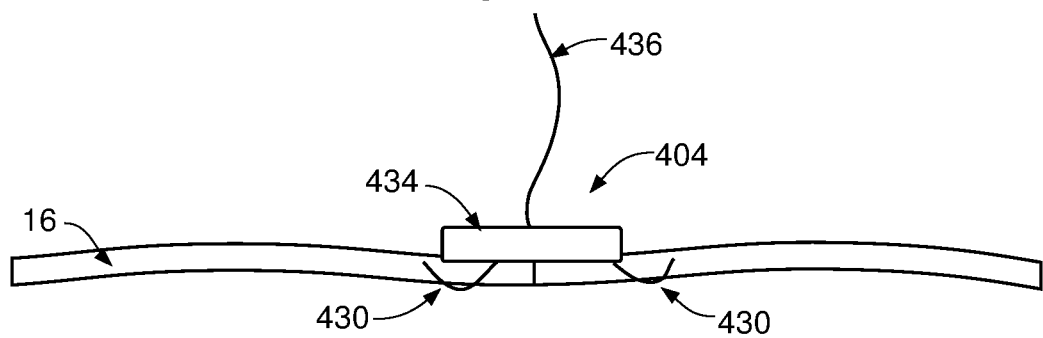

FIGS. 8A-8C depict another embodiment of an anchoring system 405 that can be used with the various ringless web embodiments of the present invention. Anchoring system 405 can be used to implant either an atrial anchor or a ventricular anchor as described herein. In one embodiment, anchoring system 405 implants an atrial anchor into annular tissue 16.

Anchoring system 405 can include a delivery catheter 438 that delivers an anchor 404 to the target tissue 16. Anchor 404 can include a head 434 and one or more barbs 430 configured to penetrate tissue 16 and retain anchor 404 on tissue 16. A suture 436 can extend from anchor 404 to connect anchor 404 to a ringless web. In operation, delivery catheter 438 is used to forcibly drive barbs 430 of anchor 404 into tissue 16. The delivery catheter 438 is then withdrawn, leaving the anchor 404 in place, with suture 436 attaching the anchor 404 to the ringless web and barbs 430 retaining the anchor 404 in the tissue 16. Although depicted as including a single suture 436, in other embodiments anchor 404 can include a connector and tensioning suture as discussed above to enable selective tensioning of a ringless web with respect to anchor 404.

Figure 9A:
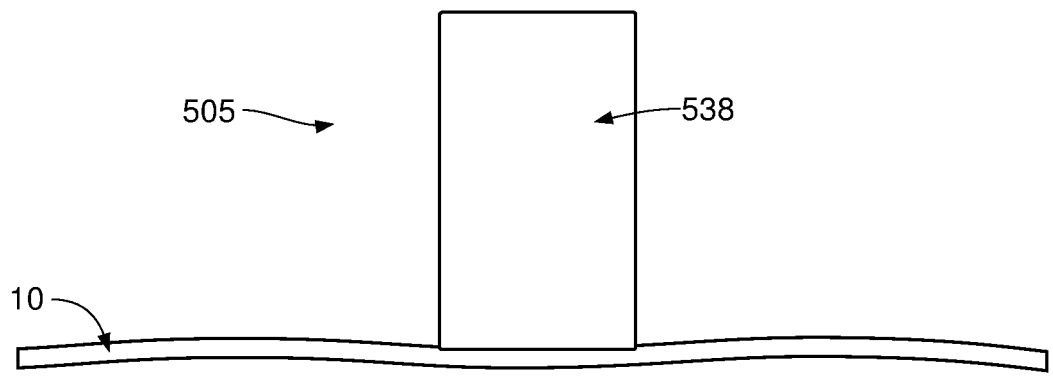
FIGS. 9A-9C depict an anchor system for a ringless web according to an embodiment of the present invention.
Figure 9B:
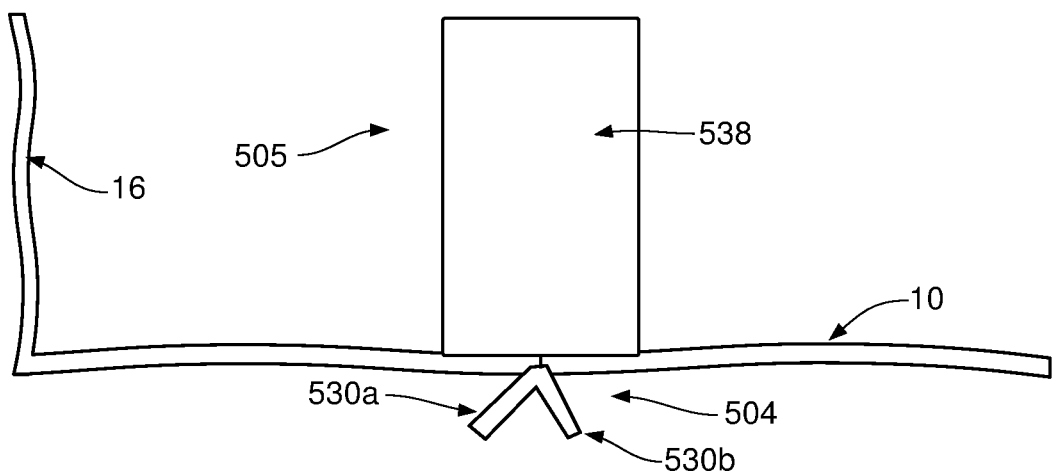
Figure 9C:
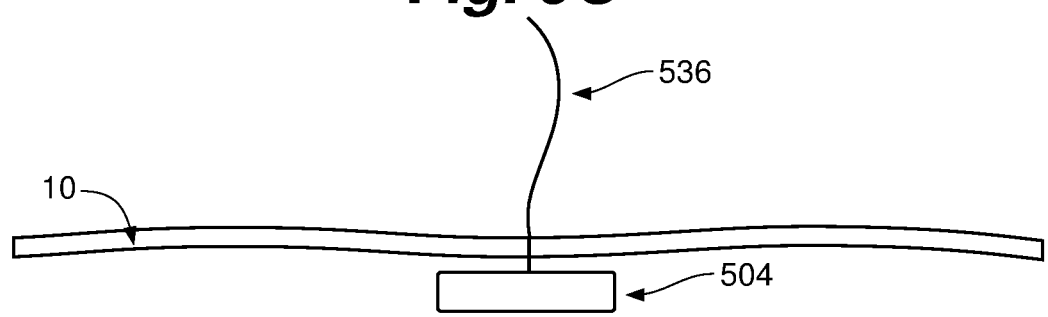

FIGS. 9A-9C depict another embodiment of an anchoring system 505 that can be used with the various ringless web embodiments of the present invention. As with the above embodiments, anchoring system 505 can be used to implant either an atrial anchor or a ventricular anchor as described herein. In one embodiment, anchoring system 505 implants an atrial anchor 504 into a leaflet 10 near the valve annulus 16. In one embodiment, the anchor can be inserted near the edge of a valve leaflet 10 approximately three millimeters from the annulus 16. Alternatively, an atrial anchoring system 505 could implant an atrial anchor 504 into the annulus 16.

Anchoring system 505 can include a delivery catheter 538 that delivers an anchor 504 to the target tissue 10. Anchor 504 can initially be configured in a generally L-shaped configuration with a first leg 530*a* and a second leg 530*b*. This allows delivery catheter 538 used to forcibly drive anchor 504 into and/or through tissue 10. The delivery catheter 538 is then withdrawn, and when tension is applied to suture 536 the anchor 504 bends around the junction between legs 530*a*, 530*b* to convert to a linear configuration that embeds the anchor 504 in, or on the opposite side of, tissue 10. Although depicted as including a single suture 536, as with the previous embodiment in other embodiments anchor 504 can include a connector and tensioning suture as discussed above to enable selective tensioning of a ringless web with respect to anchor.

Figure 10A:
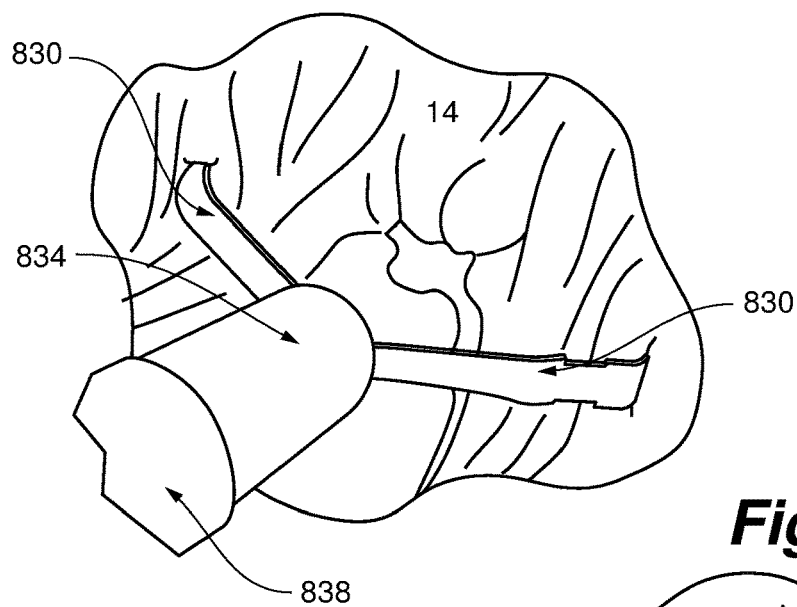
FIGS. 10A-10C depict an anchor for a ringless web according to an embodiment of the present invention.
Figure 10B:
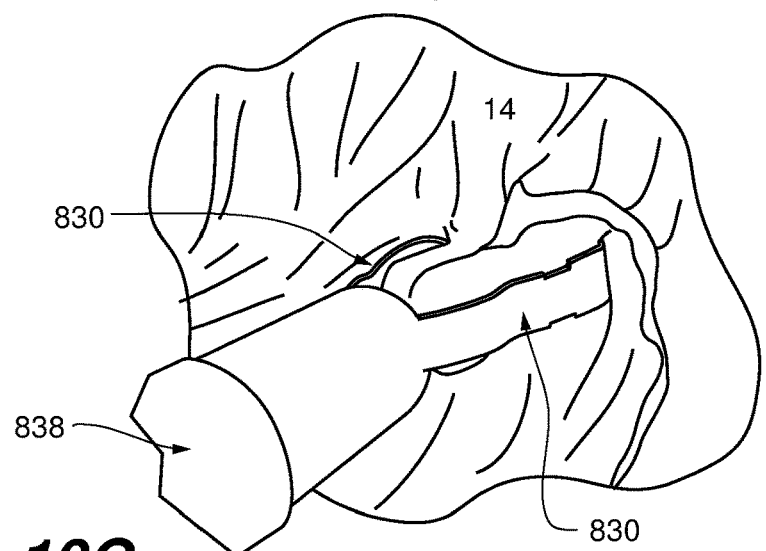
Figure 10C:
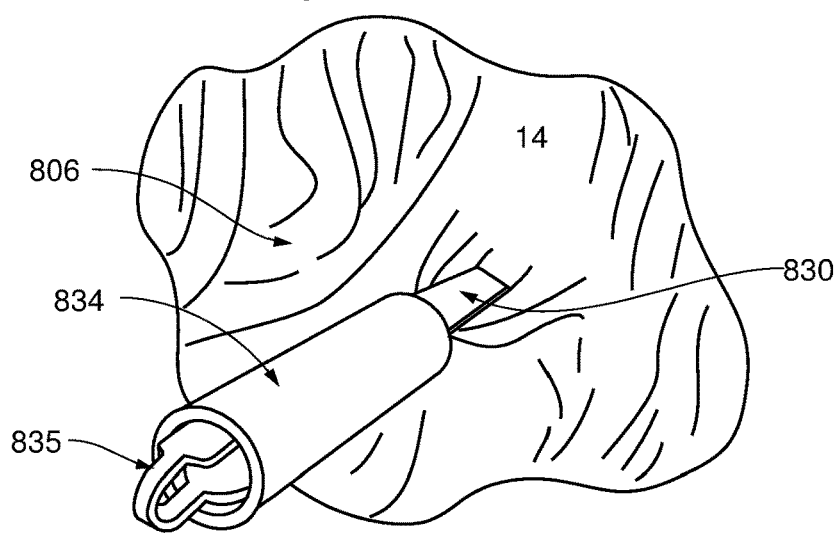

FIGS. 10A-10C depict another embodiment of an anchor 806 that can be used with any of the embodiments of the present invention, and in particular can be used as a ventricular anchor in place of the corkscrew anchor 306 described with respect to FIGS. 7A-7C. Anchor 806 includes a pair of grasping prongs 830 extending from a body 834. A catheter 838 can be used to deliver the anchor 806 to the anchor site, e.g., the papillary muscle, and can actuate the prongs to grasp the tissue 14. When it is determined that the prongs 830 have an adequate grasp on the tissue 14, they can be locked into place and the catheter withdrawn. Anchor 806 can include a connector 835 at a proximal end thereof that can receive a tensioning suture used to tension a ringless web with respect to the anchor 806 as described above.

Figure 11:
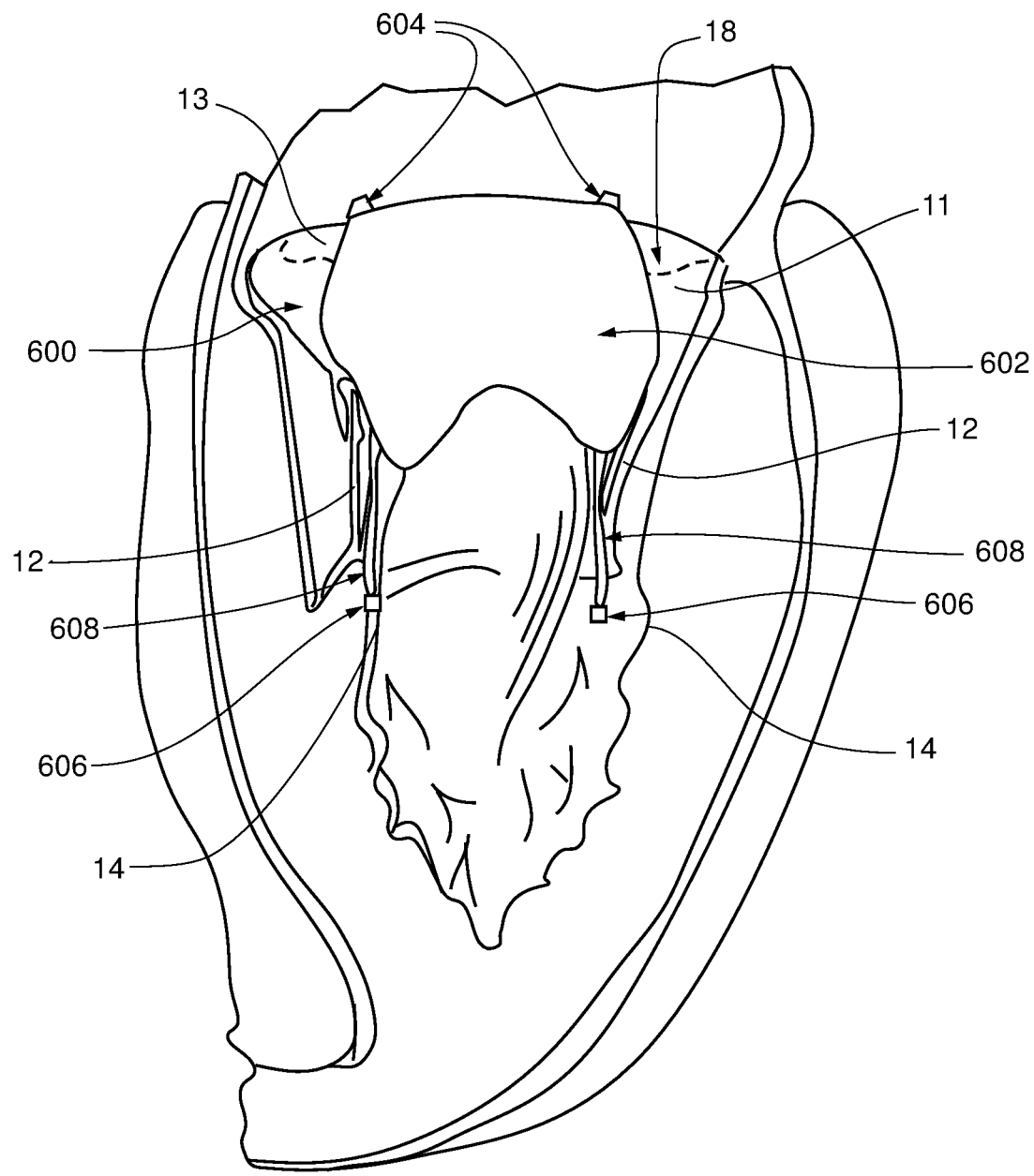
FIG. 11 is a schematic representation of a heart valve repair device according to an embodiment of the present invention deployed in the heart.

FIG. 11 schematically depicts a ringless web 600 in a final deployed position in a mitral valve of the heart according to an embodiment of the present invention. Ringless web 600 is anchored with atrial anchors 604 in or adjacent the valve annulus 16. The body 602 extends through the coaptation zone 18 between the anterior valve leaflet 11 and the posterior valve leaflet 13. The body is anchored via sutures 608 connected to ventricular anchors 606 seated in the papillary muscles 14 adjacent the natural chordae 12. Alternatively, body 602 could be anchored to the ventricular wall. By being positioned in this manner and properly tensioned as described herein, body 602 aids in promoting natural leaflet coaptation and/or prevents leaflet prolapse as discussed above. It should be noted that although ringless web 600 is depicted as including a solid body similar to the embodiment described with respect to FIG. 6, a device comprising an array of struts such as described with respect to FIGS. 4A-5B or other configuration as described above would attain a similar final position according to embodiments of the present invention.

FIG. 12 depicts a flowchart of one embodiment of procedural steps 800 taken to deploy a ringless web in the heart according to embodiments of the present invention. After the left side of the heart has been accessed, the ventricular anchors, for example, first and second ventricular anchors are sequentially inserted into heart tissue in the left ventricle at step 802. In some embodiments, a first anchor is inserted into a papillary muscle on a first side of the ventricle and a second anchor is inserted into a papillary muscle on a generally opposing side of the ventricle. At step 804, the web is positioned across the valve plane such that it is partially in the left atrium and partially in the left ventricle. The atrial anchors, for example, first and second atrial anchors, can then be seated in atrial tissue above the valve plane, such as in the valve annulus at step 806. With all four anchors in place and the web extending across the valve, at step 808 the tension placed on web from the sutures extending from one or both of the atrial and ventricular anchors can be adjusted. An ultrasound or other imaging system can then be used to confirm proper heart function and leaflet interaction with the web at the set tension at step 810. When proper heart function is confirmed, the tension can be fixed, such as by tying off the sutures connecting the one or more anchors to the web at step 812. In other embodiments, ringless web may not require tensioning. For example, web and sutures could be pre-sized for proper valve function or conformable to the valve such that the described tensioning steps are not utilized. A similar procedure as described above could be conducted to deploy a ringless web in other valves or regions of the heart.

Figure 13A:
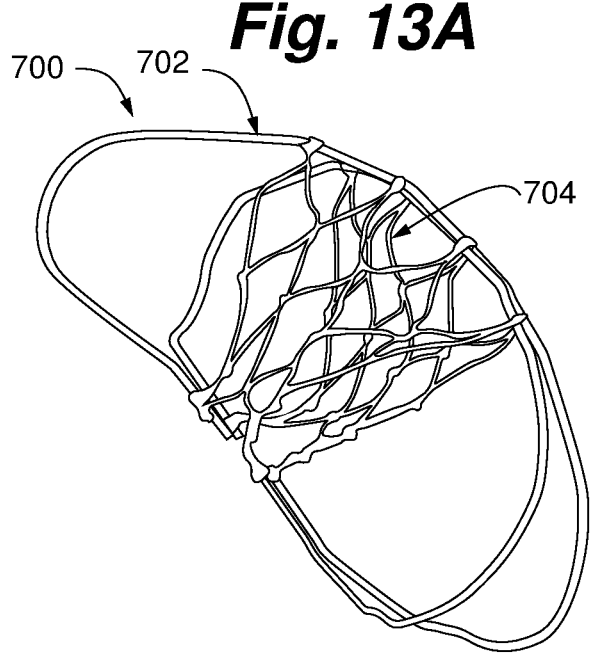
Figure 13B:
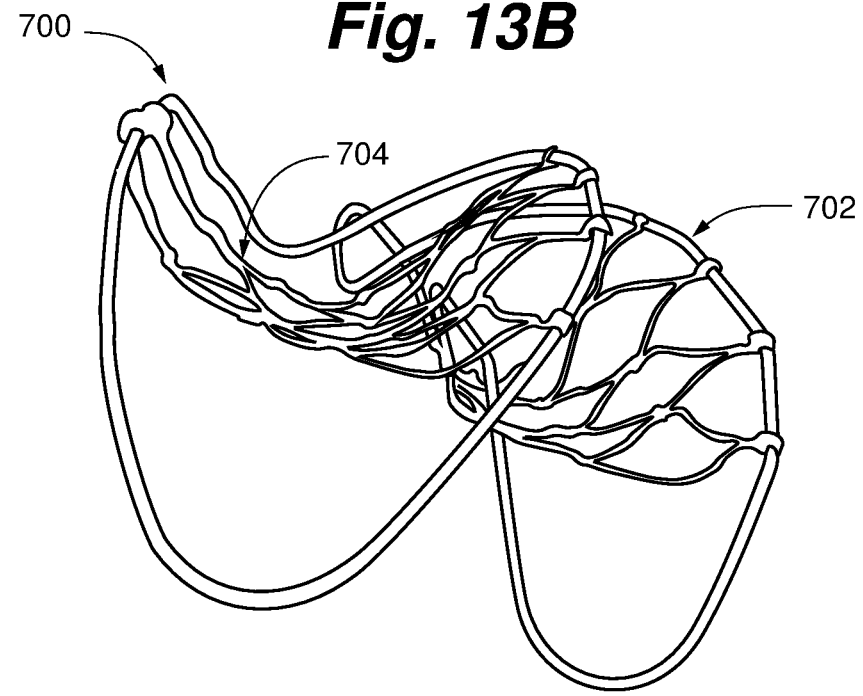

FIGS. 13A-13C depict a heart valve repair device 700 according to an alternative embodiment. Device 700 includes a generally clamshell shaped body comprising a frame 702, which is depicted in FIG. 11A in a generally open position and in FIG. 11B in a partially-closed, deployed position. A coaptation material 704 can be carried by frame 702. In various embodiments, coaptation material 704 can include, for example, a net structure, a mesh material, an array of individual strand elements, such as sutures, or some combination thereof. When deployed in the heart, an upper portion 706 of the frame 702 sits in the annulus of the valve, with the frame extending through one of the commissures of the valve and around a portion of the valve inferior to the valve plane due to the partially-closed clamshell shape of the frame 702. This causes the coaptation material to overlap a prolapsing segment of either the anterior or posterior leaflet of, e.g., the mitral valve, depending on the manner in which the device 700 is positioned. In some embodiments, the portion of the body located inferior to the valve plane is positioned between the natural chordae of the valve and the ventricular wall. Alternatively, this portion of the frame can be positioned below the coaptation zone of the leaflets, generally in front of the native chordae. In some embodiments, particularly for patients suffering from functional mitral valve regurgitation, the coaptation material could be dense mesh that generally resembles a solid material to increase the surface area for coaptation.

The values noted above are example embodiments and should not be read as limiting the scope of this invention other than as expressly claimed. Those skilled in the art will recognize that the above values may be adjusted to practice the invention as necessary depending on the physical characteristics of the patient.

Although specifically described with respect to the mitral valve, it should be understood the devices described herein could be used to treat any other malfunctioning valve, such as the tricuspid and aortic valves. Further, although not specifically described herein, it should be understood that the devices described in the present application could be implanted into the beating heart of the patient via various access approaches known in the art, including transapical approaches (through the apex of the left ventricle) and transvascular approaches, such as transfemorally (through the femoral vein). One example of a transapical access approach that could be employed with ringless webs as described herein is described in U.S. Pat. No. 9,044,221, which is hereby incorporated by reference herein. One example of a transvascular access approach that could be employed with ringless webs as described herein is described in U.S. Patent Publication No. 2013/0035757, which is hereby incorporated by reference herein. This versatility in access approach enables the access site for the procedure to be tailored to the needs of the patient.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc have been described for use with disclosed embodiments, others besides those disclosed may be utilized without exceeding the scope of the invention.

The invention claimed is:

1. A ringless web configured to be implanted into a beating heart of a patient to repair heart valve function, comprising:

a web configured to be chronically implanted in the beating heart of the patient without being attached to a ring and shaped and sized to correspond to at least one valve in the heart;

one or more ventricular anchors operably connected to the web and configured to be anchored in ventricular tissue in the heart, the web being a flexible material formed of a combination of a solid material and at least one open space therein and capable of conforming to aspects of native valve tissue of the beating heart the web further comprising a solid biocompatible material;

one or more atrial anchors operably connected to the web and configured to be anchored in atrial tissue in the heart; and a tensioning mechanism operably connected to at least one of the one or more ventricular anchors and the one or more atrial anchors, the tensioning mechanism configured to enable selective adjustment of a tension of the web with respect to the corresponding anchor such that the web is positioned across a plane of the at least one valve to repair valve function.

2. The ringless web of claim 1, wherein the web comprises an array.

3. The ringless web of claim 2, wherein the array comprises a plurality of struts.

4. The ringless web of claim 3, wherein the struts include:

a pair of ventricular struts each configured to extend from at least one of the atrial anchors through a coaptation zone of the valve and to at least one of the ventricular anchors; and one or more cross struts extending between the pair of ventricular struts.

5. The ringless web of claim 4, wherein the one or more cross struts includes at least one cross strut configured to be positioned above a plane of the valve and at least one cross strut configured to be positioned below the plane of the valve.

6. The ringless web of claim 5, wherein the solid biocompatible material is positioned between the cross strut configured to be positioned above the plane of the valve and the cross strut configured to be positioned below the plane of the valve but not positioned in the at least one open space of the web.

7. The ringless web of claim 1, wherein the web comprises a net or a mesh.

8. The ringless web of claim 7, wherein the net or mesh is connected to each of the one or more atrial anchors and each of the one or more ventricular anchors with a suture.

9. The ringless web of claim 1, wherein the tensioning mechanism comprises one or more sutures.

10. The ringless web of claim 1, wherein the web repairs valve function by restricting motion of at least one leaflet of the valve to prevent leaflet prolapse.

11. The ringless web of claim 1, wherein each of the one or more ventricular anchors has a different configuration from each of the one or more atrial anchors.

12. A ringless web configured to be implanted into a beating heart of a patient to repair heart valve function, comprising:
- a web configured to be chronically implanted in the beating heart of the patient without being attached to a ring and shaped and sized to correspond to at least one valve in the heart, the web being a flexible material formed of a combination of a solid material and at least one open space therein and capable of conforming to aspects of native valve tissue of the beating heart the web further comprising a solid biocompatible material; wherein the solid biocompatible material is located below the at least one open space of the web;
- one or more ventricular anchors operably connected to the web and configured to be anchored in ventricular tissue in the heart; and
- one or more atrial anchors operably connected to the web and configured to be anchored in atrial tissue in the heart.

13. The ringless web of claim 12, wherein the web comprises an array.

14. The ringless web of claim 13, wherein the array comprises a plurality of struts.

15. The ringless web of claim 14, wherein the struts include:
- a pair of ventricular struts each configured to extend from at least one of the atrial anchors through a coaptation zone of the valve and to at least one of the ventricular anchors; and
- one or more cross struts extending between the pair of ventricular struts.

16. The ringless web of claim 15, wherein the one or more cross struts includes at least one cross strut configured to be positioned above a plane of the valve and at least one cross strut configured to be positioned below the plane of the valve.

17. The ringless web of claim 16, wherein the solid biocompatible material is positioned between the cross strut configured to be positioned above the plane of the valve and the cross strut configured to be positioned below the plane of the valve but not positioned in the at least one open space of the web.

18. The ringless web of claim 12, wherein the web comprises a net or a mesh.

19. The ringless web of claim 18, wherein the net or mesh is connected to each of the one or more atrial anchors and each of the one or more ventricular anchors with a suture.

20. The ringless web of claim 12, wherein the web comprises a mesh.

21. The ringless web of claim 20, wherein the mesh is connected to each of the one or more atrial anchors and each of the one or more ventricular anchors with a suture.

22. The ringless web of claim 12, wherein each of the one or more ventricular anchors has a different configuration from each of the one or more atrial anchors.

* * * * *